United States Patent
Tsonev et al.

(10) Patent No.: US 7,425,263 B2
(45) Date of Patent: Sep. 16, 2008

(54) MULTI-COMPONENT, SIMULTANEOUS, INDEPENDENT MULTI-GRADIENT SYSTEM FOR LIQUID CHROMATOGRAPHY

(75) Inventors: Latchezar I. Tsonev, Rockville, MD (US); Allen G. Hirsh, Rockville, MD (US)

(73) Assignee: Cryobiophysica, Rockville, MD (US)

( * ) Notice: Subject to any disclaimer, the term of this patent is extended or adjusted under 35 U.S.C. 154(b) by 0 days.

(21) Appl. No.: 11/847,303

(22) Filed: Aug. 29, 2007

(65) Prior Publication Data

US 2008/0053830 A1  Mar. 6, 2008

Related U.S. Application Data

(60) Provisional application No. 60/840,688, filed on Aug. 29, 2006.

(51) Int. Cl.
*B01D 15/08* (2006.01)
(52) U.S. Cl. .............. 210/198.2; 210/656; 210/101
(58) Field of Classification Search .............. 210/635, 210/656, 659, 101, 198.2
See application file for complete search history.

(56) References Cited

U.S. PATENT DOCUMENTS

| | | | | |
|---|---|---|---|---|
| 3,712,513 | A * | 1/1973 | Ashmead et al. | 222/134 |
| 5,089,124 | A * | 2/1992 | Mahar et al. | 210/198.2 |
| 6,221,250 | B1 * | 4/2001 | Stafstrom | 210/656 |
| 7,138,051 | B2 * | 11/2006 | De Lamotte | 210/198.2 |
| 2002/0153312 | A1 * | 10/2002 | Gjerde et al. | 210/635 |
| 2007/0144973 | A1 * | 6/2007 | Tsonev et al. | 210/659 |

OTHER PUBLICATIONS

Therkorn, "International Search Report," from PCT/US2007/077162, 2 pages, United States Patent and Trademark Office, Alexandria, Virginia (mailed Jun. 4, 2008).
Therkorn, "Written Opinion," from PCT/US2007/077162, 3 pages, United States Patent and Trademark Office, Alexandria, Virginia (mailed Jun. 4, 2008).

* cited by examiner

*Primary Examiner*—Ernest G Therkorn
(74) *Attorney, Agent, or Firm*—Cooley Godward Kronish, LLP

(57) ABSTRACT

Systems and methods for separating charged molecules on the basis of their differential electrostatic binding to a charged stationary phase comprise controlling the creation of simultaneous independent or dependent pH and additive gradients.

6 Claims, 6 Drawing Sheets

DIAGRAM OF SIMULTANEOUS GENERALIZED PISEP GRADIENTS WITH TWO ADDITIVE COMPONENTS

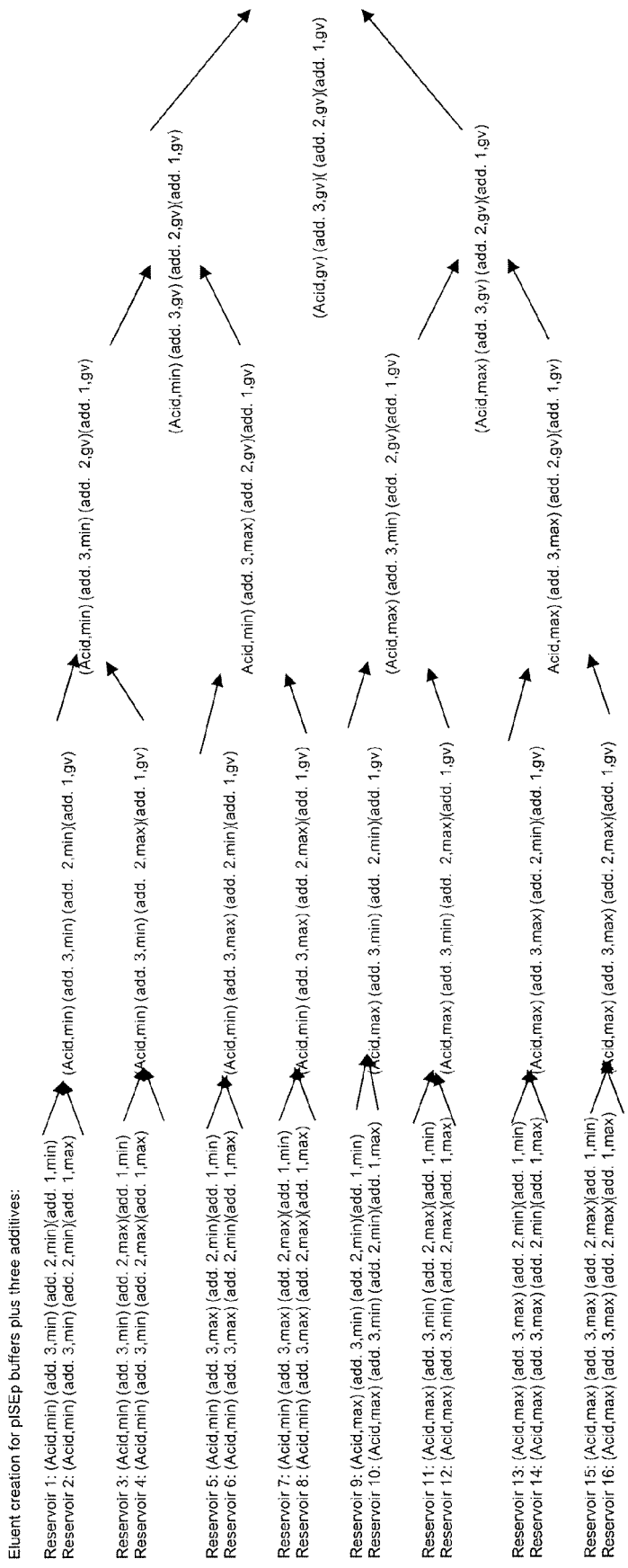

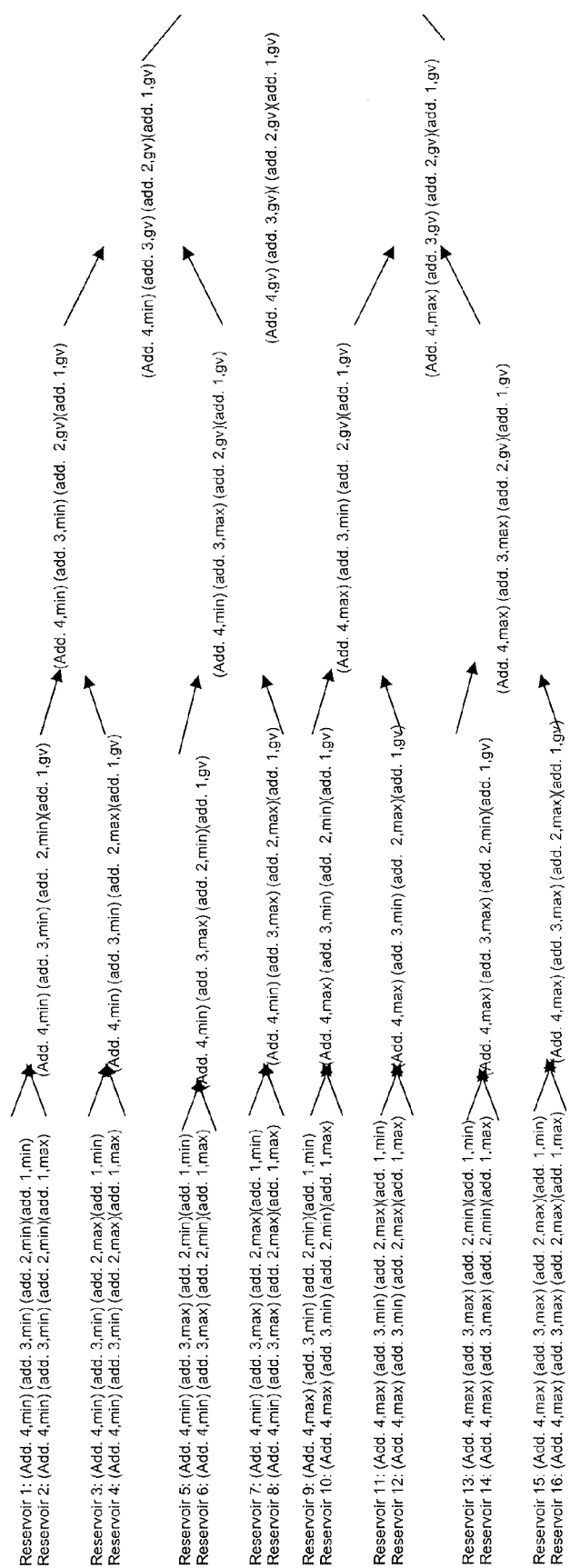

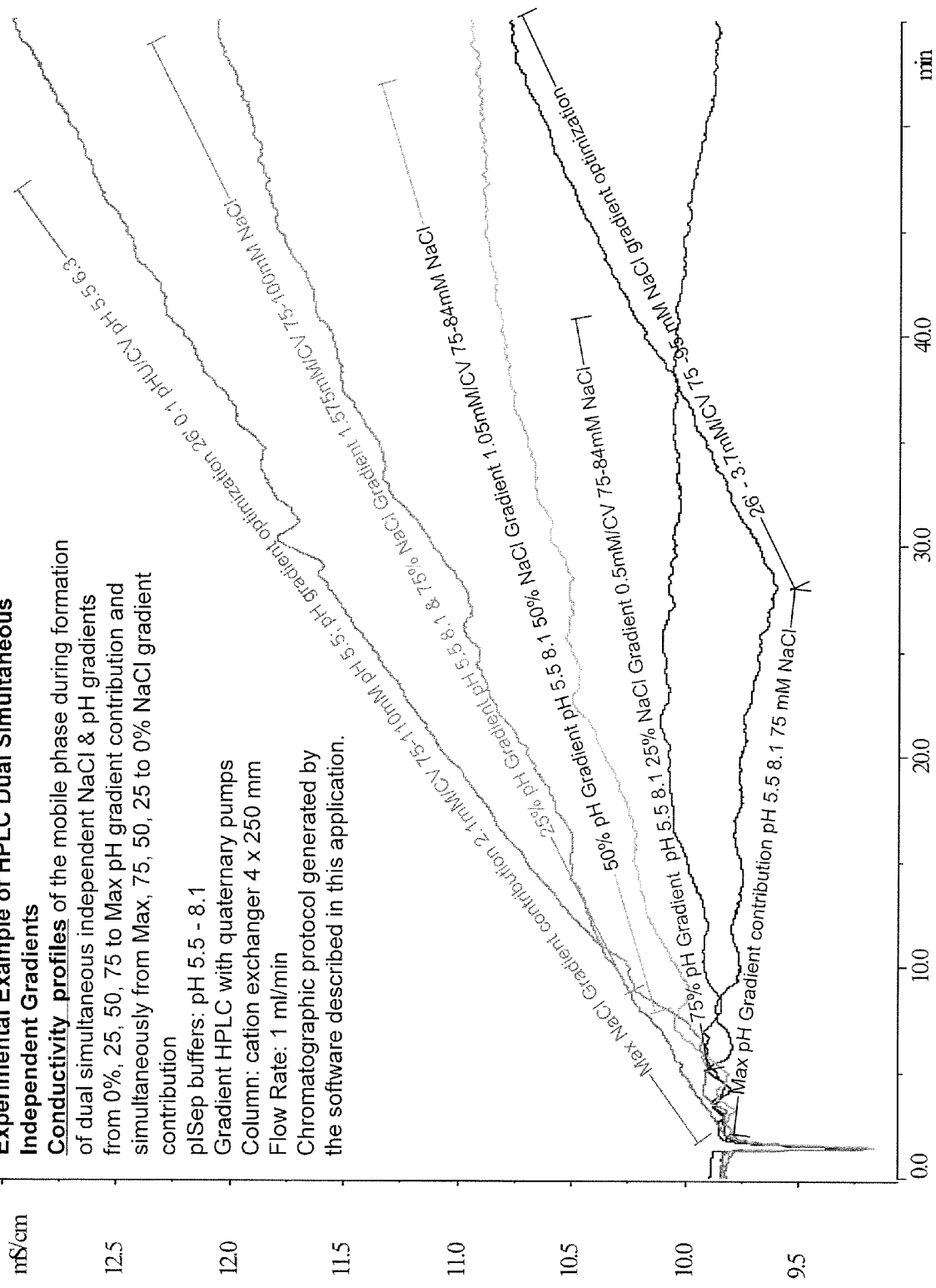

MULTI-COMPONENT, SIMULTANEOUS, INDEPENDENT MULTI-GRADIENT SYSTEM FOR LIQUID CHROMATOGRAPHY

CROSS-REFERENCE TO RELATED APPLICATIONS

This application claims the benefit of U.S. Provisional Application No. 60/840,688, filed Aug. 29, 2006.

BACKGROUND OF THE INVENTION

About thirty years ago, Sluyterman et al pioneered chromatofocusing, a new liquid chromatography method. It consists of descending retained pH gradients created by complex interactions between multi-component mobile phase buffers (polybuffers) and weak anionic stationary phases. Separation of charged macromolecules by differential binding to charged stationary phases by titration of the charges on the macromolecular surface as the result of varying pH resolves molecular species much better than shielding of binding to charged stationary phases by increasing salt concentration. Thus, it was hoped that chromatofocusing would widely supplant traditional salt elution, but that has not occurred. In large measure this is because chromatofocusing was discovered to have several serious shortcomings. In chromatofocusing, for each pH range over which one wishes to create a gradient, one has to create a separate buffer solution. For any given pH range over which the gradient is formed, the slope of the gradient in the column is proportional to that pH range, thus precluding controlled variations of the slope during repetitive formation of gradients having the same range. No single formulation of the polybuffers could maintain good buffering capacity over more than 3 pH units, necessitating the commercialization of three different formulations by the manufacturer, Pharmacia, to cover the pH ranges from 11 to 8, 9 to 6, and 7 to 4. The polybuffers are composed of a complex mix of small polyelectrolytes, some of which frequently bind strongly to proteins targeted for isolation, and are very expensive. Thus they are essentially never used in preparative protein purification. Despite these shortcomings, the methodology has found a renewed market position as the first dimension of the Beckman-Coulter ProteomeLab™ PF 2D Protein Fractionation System. This has come about because, despite the difficulties outlined above, uncontrolled retained pH gradients are still significantly better at fractionating proteins from complex mixtures than isocratic pH salt gradients are.

In the intervening years since Sluyterman et al's initial work, numerous attempts have been made to address chromatofocusing's shortcomings. Virtually all of them have consisted of relatively simple buffer combinations designed to interact with weak ion exchange stationary phases to create retained pH gradients on the stationary phase. In a few instances the reference buffers have been mixed externally, but no successful method to control the pH by purely external manipulations has been forthcoming. Generally, those attempting to improve on chromatofocusing have made the assumption that interactions between the buffers and the stationary phase that lead to complex and hard to control changes in eluant pH are inevitable and thus purely externally determined pH gradients are not practically achievable. The result has been the absence of patented marketable systems for producing fully controllable pH liquid chromatography gradients over wide pH ranges. Thus, a number of important problems remain unsolved: 1) software driven creation of multi-step pH gradients with a range of both positive and negative slopes limited only by the mixing accuracy of modern liquid chromatography systems; 2) the software driven ability to vary the slope of a pH gradient arbitrarily throughout a chromatographic separation independent of the initial and final pH and without changing the buffer chemistry with each slope change; 3) creation of controlled pH gradients on both anionic and cationic stationary phases; 4) software driven control of gradients of additional constituents (additives) to the eluting buffer such as nonionic detergents, organic solvents, salts etc. that do not significantly interfere with the formation of the pH gradients such that two or more independent, simultaneous gradients can be developed and controlled on the same stationary phase (s); 5) relatively inexpensive simple mobile-phase compositions with few buffer components while also solving problems #1-4; 6) buffer components of the mobile-phase that do not bind to proteins while also solving problems #1-5; and 6) provide mobile eluant phases that have hydrophobic, polar, and electrostatic properties allowing formation of efficient and independent simultaneous controllable gradients to fully utilize the selective and resolving capabilities of mixed mode stationary phases containing simultaneously ionizable groups and hydrophobic groups and stable over a broad pH range e.g. 2-12.

SUMMARY OF THE INVENTION

In one embodiment, the present invention provides novel methods for the liquid chromatographic separation of charged molecules such as proteins according to their apparent isoelectric points on a charged stationary phase. In a second embodiment, the present invention provides a novel chromatography system for use with low or high pressure liquid chromatography that comprises a multidimensional gradient system for separating charged molecules according to their apparent isoelectric points on anionic stationary phases, their apparent isoelectric points on cationic stationary phases, and their hydrophobicity. In the following, reference is made to components of a liquid chromatographic system that are mixed to form gradients in the concentration of each component.

The multi-component simultaneous independent gradient system (MSIGS) described here systematically addresses and solves problems frequently encountered during separations of charged, polar, nonpolar, small, and large molecules by electrostatic interaction chromatography (ion exchange chromatography with salt and pH gradients), hydrophobic interaction chromatography, reversed phase chromatography, affinity chromatography etc. MSIGS comprises the use of a combination of a small number of low molecular weight poly-ionic organic buffer species with overlapping pKas over a broad pH range from at pH 2 or lower to pH 12 or higher. The acidic and alkaline reference solutions utilized to form external pH gradients have almost identical compositions except for small amounts of strong acids or bases used to adjust their initial pH when the entire pH range is to be used. Consequently they have low and nearly identical ionic strength. The pH gradients are formed by mixing the acidic and alkaline buffers external to the column containing the stationary phase according to equations that determine the proportions of each buffer as a function of the pH. Furthermore, another embodiment of this system is a buffer chemistry that does not interact strongly with strong anionic and cationic ion exchange resins so that the externally determined gradients are not skewed by passage through the stationary phase. This has allowed construction of a software implementation of an on-demand pH gradient formation as part of this system. Thus, the MSIGS uniquely solves the following problems: 1) creation of pH gradients with a range of both positive and negative slopes limited only by the mixing accuracy of modern liquid chromatographic systems; 2) the ability to vary the slope of the pH gradient arbitrarily throughout a chromatographic separation independent of the initial and final pH and without changing the buffer chemistry with each slope change; 3) creation of controlled pH gradients on both anionic and cationic stationary phases; 4) relatively inexpensive buffer components; and 5) buffer components that do not bind to proteins.

The MSIGS is designed to allow the control of more than one gradient simultaneously, and at the same time independently developing on one column, several parallel columns, or multiple columns connected in series forming a tandem system. It is thereby able to accomplish separations unavailable to currently marketed gradient methodologies. As an example, it can be shown that by carrying out simultaneous salt and pH gradients where the slope of the salt gradient is varied while maintaining a pH gradient with non-zero slope, certain problematic isoforms of monoclonal antibodies (polyglycosylated proteins) can be readily separated, whereas pH gradients at isocratic salt and salt gradients at isocratic pH are unable to resolve these isoforms. Because the developed gradients are independent of each other, a chromatographer can easily create virtually unlimited numbers of usefully unique chromatographic protocols. This flexibility is presently unavailable from any other literature source or liquid chromatographic system manufacturer. A series of fundamental problems, presently unaddressed by commercial producers of chromatographic systems is thereby solved:

1) simultaneously separating target analytes in complex mixtures of molecules based on the sum of their hydrophobic binding energies plus their electrostatic binding energies on mixed-mode stationary phases; 2) effectively separating, on ion exchange and mixed mode stationary phases, target analytes in low aqueous solubility complex mixtures such as membrane protein isolates by simultaneously controlling gradients of pH and solubilizing chaotropic agents such as urea; 3) providing a compelling reason to create new mixed-mode stationary state compositions with a range of hydrophobic and ionic binding sites and stability over wide pH ranges e.g. 2-12; and 4) allowing formation of simultaneous, independent gradients of eluent components not directly involved in buffering pH, such as methanol-acetonitrile or salt-acetonitrile for improved separation of analytes on hydrophobic interaction and reverse phase columns.

BRIEF DESCRIPTION OF THE DRAWINGS

FIG. 3 is a diagrammatic representation of simultaneous generalized pISep plus three additive gradients.

FIG. 4 is a diagrammatic representation of simultaneous additive gradients.

FIG. 5 is an experimental example of HPLC dual simultaneous independent gradients. FIG. 5B shows conductivity profiles.

DETAILED DESCRIPTION OF THE INVENTION

In the following embodiments of the invention, reference is made to a particular set of buffers denominated as pISep buffers. pISep buffers are buffer compositions characterized by buffering components having overlapping pKa's throughout a target range of pH, and wherein the molar proportion of each component remains constant or varies throughout the transition between an initial pH and a final pH, wherein each buffering component contains at least one functionality selected from the group consisting of amino, amido, imino, imido, carboxylic, sulfonic, phosphoric and phosphonic. Furthermore, each buffering component is present in a concentration of 0.001 mM to 1000 mM. To generate pH gradients controlled by software, external to a chromatographic column(s), an acid pISep buffer is prepared by titrating the pISep buffers to a lower pH limit by using a strong acid, and a complimentary basic pISep buffer is prepared by titrating the pISep buffers to an upper pH limit by using a strong base. The algorithms described below refer to controlling the mixing of the acidic pISep buffer and the basic pISep buffer to attain a target pH anywhere within the target range of pH. A preferred composition of pISep buffers consists of buffering components comprising piperazine, 1-methyl piperazine, triethanolamine, bis-tris propane and formic acid.

Throughout this document reference is made to components 1, 2, . . . n. In all such cases a component 0 is implied, acting as a solvent. In all cases a minimum concentration of any one or more component can be chosen to be as small as zero. An example of this would be a water-methanol-acetonitrile system with water as the solvent. Thus, in this water-methanol-acetonitrile system an acceptable set of concentrations could be a minimum methanol concentration of 0% wt./wt., a maximum methanol concentration of 40% wt./wt.; a minimum acetonitrile concentration of 0% wt./wt., a maximum acetonitrile concentration of 60% wt./wt; and a minimum water(solvent) concentration of 0% wt./wt., a maximum water concentration of 100% wt./wt.

The acronym LC used herein refers to a liquid chromatograph.

Figure 1:
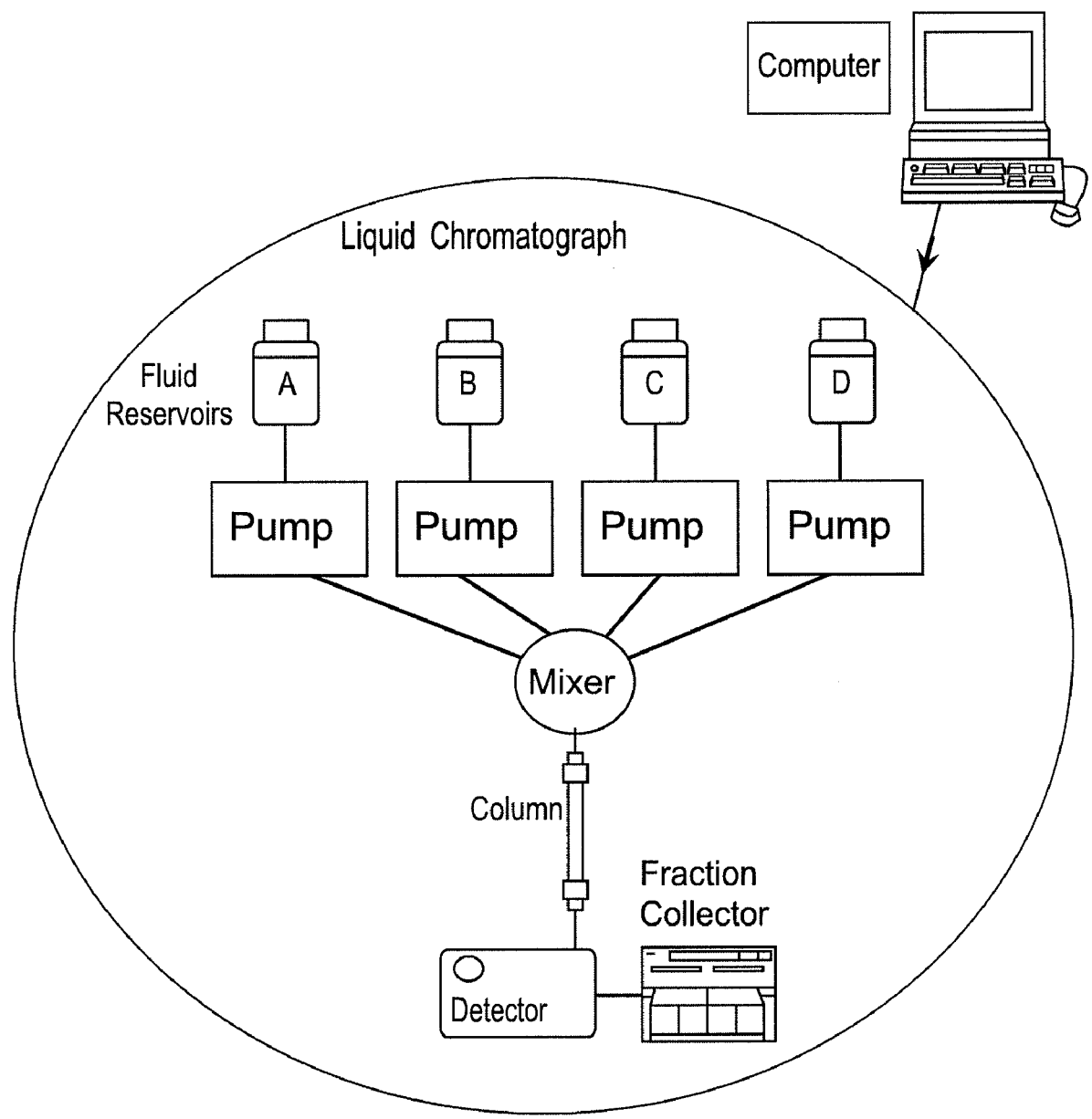
FIG. 1 is a diagrammatic representation of a liquid chromatographic system or apparatus which can be used to implement the MSIGS the present invention.

The algorithms and software disclosed herein can be implemented on conventional liquid chromatographic equipment, e.g. a liquid chromatograph comprising a computer-controlled pump having four or more channels, and associated computer-controlled valves connected to one or more chromatographic columns, equipped with conventional detectors (e.g., UV, infrared, fluorescence, refractive index, conductivity, etc.) and/or fraction collection devices. The various components, above, can be interconnected according to conventional practice in the art, for example using metallic tubing. In one embodiment, the methods of the present invention are carried out on a chromatographic device as shown in FIG. 1.

Figure 2:
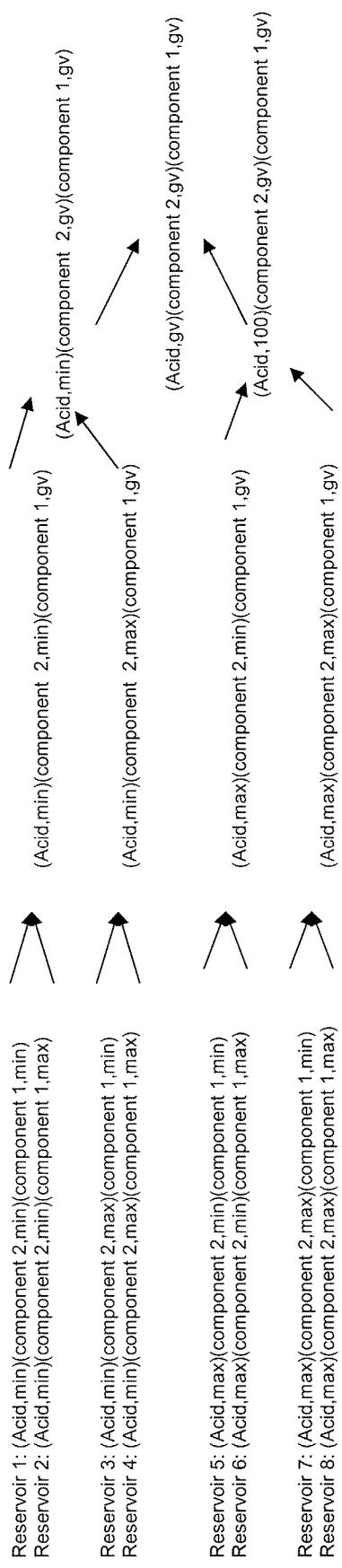
FIG. 2 is a diagrammatic representation of simultaneous generalized pISep gradients with two added to components.
Figure 5A:
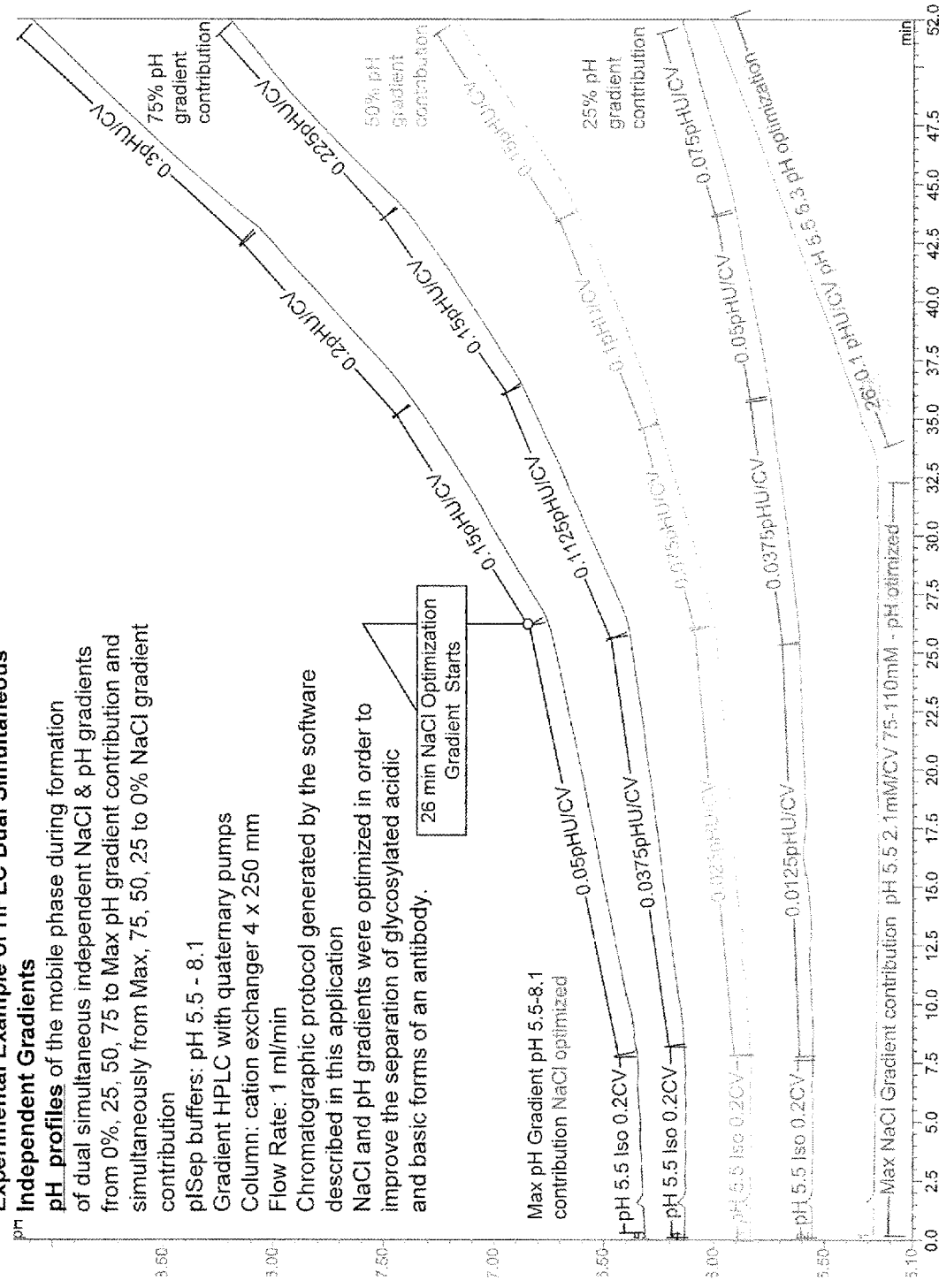
FIG. 5A shows pH profiles.

FIG. 2 is a flow diagram for a controlled external pH gradient with two simultaneous independent gradients of additives, labeled 1 and 2 (with the pH gradient implicitly designated #3). Conceptually, it is easiest to start on the right, with the last mixing step, and analyze the schema backwards. In the final mixing step the gradient determined levels of both components 1 and 2 are present in both efflux streams (gv I.e. gradient value). The acid and basic solutions' flow magnitudes are equal to the manifold designated fractions of the total flow value necessary to achieve the gradient designated pH. At the previous mixing step component one is mixed in all four efflux streams but component 2 is either at its maximum in each of an acidic and a basic stream, or at minimum concentration in the complementary pair of streams. The pumping rate for each stream will then be a fraction of the acidic or, alternatively, basic flow total apportioned according to what fraction of minimum component 2 concentration eluent must be mixed with maximum component 2 concentration eluent to achieve the gv of component 2. At the first level each of the four eluent flows necessary to attain gv for component 2 is further divided into two incoming flows (total of eight flows) based on the apportionment of flow fractions derived from to what fraction of minimum component 1 concentration eluent must be mixed with maximum of component 1 concentration eluent to achieve the gv of component 1 for each of the four pairs. This determines the pumping rate for the efflux from each of the eight reservoirs.

FIG. 3 is the flow diagram for a controlled external pH gradient with three simultaneous independent gradients of additives, labeled 1-3 (with the pH gradient implicitly designate #4). Conceptually, it is easiest to start on the right, with the last mixing step, and analyze the schema backwards. In the final mixing step the gradient determined levels of both components 1 and 2 are present in both efflux streams (gv I.e. gradient value). The sum of the acid and the sum of the basic solutions' flow magnitudes are each separately equal to the manifold designated fractions of the total flow value necessary to achieve the gradient designated pH. At the previous mixing step component 1 and 2 are mixed in all four efflux streams but component 3 is either at its maximum in each of an acidic and a basic stream, or at minimum concentration in the complementary pair of streams. The pumping rate for each stream will then be a fraction of the acidic or, alternatively, basic flow total apportioned according to what fraction of the minimum concentration of component 3 eluent must be mixed with (1–that fraction) of maximum concentration component 3 eluent to achieve the gv of component 3. At the next level each of the four eluent flows necessary to attain gv for component 3 is further divided into two incoming flows (total of eight flows) based on the apportionment of flow fractions derived from to what fraction of the minimum concentration of component 2 eluent must be mixed with maximum concentration of component 2 eluent to achieve the gv of component 2 for each of the four pairs. This pattern is repeated for component 1 determines the pumping rate for the efflux from each of the sixteen reservoirs.

FIG. 4 is the flow diagram for a control of simultaneous independent gradients of four additives, labeled 1-4. Conceptually, it is easiest to start on the right, with the last mixing step, and analyze the schema backwards. In the final mixing step the gradient determined levels of components 1-3 are present in both efflux streams (gv I.e. gradient value). The pumping rate for each stream will then be the fraction of the minimum concentration of component 4 eluent that must be mixed with (1–that fraction) of maximum concentration component 4 eluent to achieve the gv of component 4. At the previous mixing step component 1-2 are mixed in all four efflux streams but component 3 is either at its maximum in each of two streams, or at minimum concentration in the complementary pair of streams. At the next level each of the four eluent flows necessary to attain gv for component 3 is further divided into two incoming flows (total of eight flows) based on the apportionment of flow fractions derived from to what fraction of the minimum concentration of component 2 eluent must be mixed with maximum concentration of component 2 eluent to achieve the gv of component 2 for each of the four pairs. This pattern repeated for component 1 determines the pumping rate for the efflux from each of the sixteen reservoirs.

pH Gradient on One or More Columns

In another embodiment of the invention, there is provided a system or method for chromatographically separating charged molecules having different isoelectric points, comprising:

a computer comprising a CPU, dynamic memory, and static memory and software that controls the operation of a multi-pump LC system; and at least two independent fluid delivery channels A and B, having fluid delivery rates that are independently controlled by software running on a computer; and a reservoir, RA containing an acidic buffer selected from the group consisting of the class of acidic pISep buffers; a reservoir, RB, containing a basic buffer selected from the group consisting of the class of basic pISep buffers; a pump A that controls the efflux of acidic buffer from reservoir RA and a pump B that controls the efflux of basic buffer from reservoir RB; and at least one column containing stationary phases selected from the group of stationary phases consisting of strong anionic exchange stationary phases, strong cationic exchange stationary phases, weak anionic exchange stationary phases, weak cationic exchange stationary phases, hydrophobic stationary phases, and mixtures of hydrophobic and ion exchange stationary phases (mixed mode); and software configured such that if there is at least one stationary phase then software controls and directs the LC to perform:

a system of chromatographically separating charged molecules having different isoelectric points, comprising:

applying and binding the molecules to be separated to a stationary phase perfused with a pISep solvent at the initial pH; and supplying to the stationary phase an eluent with a variable pH starting at the initial pH formed from the continuous mixing of (i) a pISep buffer solution at a predetermined acidic pH pumped out from reservoir RA with (ii) a pISep buffer solution at a predetermined alkaline pH pumped out from reservoir RB, wherein the mixing proportions of the solutions from the RA (A %) and RB(100-A %) reservoirs vary to maintain an unretained pH gradient with an externally defined slope; and the mixing proportions are determined by an equation that specifies the relationship between the % acidic pISep buffer (A %) in the mobile phase and the pH:A %=F(pH); and collecting the charged molecules until a predetermined final pH is reached, wherein each of the molecules consecutively elutes from the stationary phase at where is the pH dependent retention time of each charged molecule.

One Column pH Gradient Plus One Component at Isocratic Concentration

In another embodiment of the invention, there is provided a method or system for chromatographically separating charged molecules having different isoelectric points, comprising:

a computer comprising a CPU, dynamic memory, and static memory and software which controls the operation of a multi-pump chromatographic separation system; and at least two independent fluid delivery channels A and B, whose fluid delivery rate is independently controlled by software running on a computer; and a reservoir, $R_A$ containing an acidic buffer selected from the group consisting of the class of acidic pISep buffers, and one isocratic component (a component at a constant concentration, hereafter designated as an IC) selected from the group of components consisting of nonionic detergents, ionic detergents, polar organic molecules, nonpolar organic molecules, acids, bases, neutral salts, acidic salts and basic salts, and a reservoir, $R_B$, containing a basic buffer selected from the group consisting of the class of basic pISep buffers, and an IC; a pump A that controls the efflux of acidic buffer from reservoir $R_A$ and a pump B that controls the efflux of basic buffer from reservoir $R_B$; and at least one column containing a stationary phase selected from the group of consisting of strong anionic exchange stationary phases, strong cationic exchange stationary phases, weak anionic exchange stationary phases, and weak cationic exchange stationary phases; and software configured such that if there is one column of stationary phases, then the software controls and directs the LC to perform:

a method of chromatographically separating charged molecules having different isoelectric points, comprising:

applying and binding the charged molecules to be separated to an anionic or cationic ion exchange stationary phase, perfused with a solvent comprising at least one buffering component and an IC at a predetermined initial pH at which the ion exchange stationary phase has a charge opposite that of the charged molecules; and supplying to the ion exchange stationary phase an eluent having a variable pH starting at the initial pH formed from the continuous mixing of (i) a solution at a predetermined acidic pH containing the at least one buffering component, and an IC pumped out from reservoir $R_A$ with (ii) a solution at a predetermined alkaline pH containing the at least one buffering component and an IC pumped out from reservoir $R_B$, wherein the mixing proportions of the solutions from the $R_A$ and $R_B$ reservoirs vary to maintain an unretained pH gradient with an externally defined slope; and collecting the charged molecules until a predetermined final pH is reached, wherein each of the molecules consecutively elutes from the ion exchange stationary phase at its effective isoelectric point.

One Column Two Simultaneous Independent Gradients of Two Components

In an embodiment of the invention, there is provided a method or system for chromatographically separating charged or uncharged molecules having different binding affinities for a stationary phase, comprising:

a computer comprising a CPU, dynamic memory, and static memory and software that controls the operation of a multi-pump LC separation system; and at least four independent fluid delivery channels A, B, C, and D having fluid delivery rates that are independently controlled by software running on a computer; and a reservoir, $R_A$ containing a mobile phase with a minimum concentration of component 1, $E_{1,min}$, and a minimum concentration of component 2, $E_{2,min}$, and a reservoir, $R_B$, containing a mobile phase with a maximum concentration of component 1, $E_{1,max}$, and a minimum concentration of component 2, $E_{2,min}$; and a reservoir, $R_C$, containing a mobile phase with a minimum concentration of component 1, $E_{1,min}$, and a maximum concentration of component 2, $E_{2,max}$; and a reservoir, $R_D$, containing a mobile phase with a maximum concentration of component 1, $E_{1,max}$, and a maximum concentration of component 2, $E_{2,max}$; a pump A that controls the efflux of mobile phase from reservoir $R_A$ at rate $r_A$ and a pump B that controls the efflux of mobile phase from reservoir $R_B$ at rate $r_B$ and a pump C that controls the efflux of mobile phase from reservoir $R_C$ at rate $r_C$ and a pump D that controls the efflux of mobile phase from reservoir $R_D$ at rate $r_D$; and if $$X_1 = \frac{E_{1,max} - E_1}{E_{1,max} - E_{1,min}} \text{ and } X_2 = \frac{E_{2,max} - E_2}{E_{2,max} - E_{2,min}}$$

and $r_{total} = r_A + r_B + r_C + r_D$ then the software determines the concentrations of component 1, $E_1$, and component 2, $E_2$, at any time or column volume by directing pump A to pump at rate $r_A = X_1 * X_2 * r_{total}$, pump B to pump at rate $r_B = (1-X_1) * X_2 * r_{total}$, pump C to pump at rate $r_C = X_1 * (1-X_2) * r_{total}$, and pump D to pump at rate $r_D = (1-X_1) * (1-X_2) * r_{total}$ onto the stationary phase after mixing of the flows from pumps A, B, C and D:

a) eluting the charged or uncharged molecules, each of which consecutively elutes from the stationary phase at a concentration $E_1$ and $E_2$ such that $$\int \frac{dt}{T_R} = 1$$

where $T_R$ is the component concentration dependent retention time; and b) collecting the charged or uncharged molecules, each of which consecutively elutes from the stationary phase at a concentration $E_1$ and $E_2$ such that $$\int \frac{dt}{T_R} = 1$$

where $T_R$ is the component concentration dependent retention time: and c) repeating steps a)-b) as deemed necessary to separate all of the molecular species of interest.

Two Hydrophilic Columns pH Gradient Plus One Component at Isocratic Concentration (Configuration A)

In still another embodiment of the invention, there is provided a method or system for chromatographically separating charged molecules having different isoelectric points, comprising:

a computer comprising a CPU, dynamic memory, and static memory and software which controls the operation of a multi-pump LC separation system; and at least two independent fluid delivery channels A and B, whose fluid delivery rate is be independently controlled by software running on a computer; and a reservoir, $R_A$ containing an acidic buffer selected from the group consisting of the class of acidic pISep buffers and an IC; and a reservoir, $R_B$, containing a basic buffer selected from the group consisting of the class of basic pISep buffers and an IC; a pump A that controls the efflux of acidic buffer from reservoir $R_A$ and a pump B that controls the efflux of basic buffer from reservoir $R_B$; and at least two columns containing stationary phases selected from the group of stationary phases consisting of strong anionic exchange stationary phases, strong cationic exchange stationary phases, weak anionic exchange stationary phases, and weak cationic exchange stationary phases; and software configured such that if there are two columns of stationary phases then software directs and controls the LC to perform:

a combined external pH gradient LC method for separating charged molecules having different isoelectric points, comprising:

applying and binding the charged molecules to be separated to a first column containing a cationic or anionic ion exchange stationary phase perfused with an eluent comprising at least one buffering component and an IC at a predetermined initial pH at which the ion exchange stationary phase has a charge opposite that of the charged molecules;

connecting in series after the first column a second column containing an ion exchange stationary phase of the opposite charge to the stationary phase contained in the first column and equilibrating the ion exchange stationary phases contained in the first and second columns at the initial pH;

supplying to the ion exchange stationary phase contained in the first column an eluent with a variable pH starting at the initial pH formed from the continuous mixing of (i) a solution with predetermined acidic pH containing the at least one buffering component and an IC pumped out from reservoir $R_A$ with (ii) a solution at a predetermined alkaline pH containing the at least one buffering component and an IC pumped out from reservoir $R_B$, wherein the mixing proportions of the solutions from the $R_A$ and $R_B$ reservoirs vary to maintain an unretained pH gradient with an externally defined slope;

a) eluting the charged molecules, each of which consecutively elutes from the ion exchange stationary phase contained in the first column at its effective isoelectric point until a predetermined final pH is reached;

b) directing for secondary separation the resulting effluent containing the consecutively eluted charged molecules from the first column into the ion exchange stationary phase contained in the second column and;

c) binding the charged molecules that are oppositely charged to the ion exchange stationary phase contained in the second column until the predetermined final pH is reached;

d) disconnecting, as directed by software, the first column from the second column;

e) reversing the pH gradient perfusing the ion exchange stationary phase contained in the second column to develop from the predetermined final pH to a second predetermined final pH; and f) collecting the charged molecules wherein each of the molecules consecutively elutes from the ion exchange stationary phase contained in the second column at its effective isoelectric point until the second predetermined final pH is reached; and g) optionally reconnecting by direction of software in series after the first column a second column containing an ion exchange stationary phase of the opposite charge to the stationary phase contained in the first column and equilibrating the ion exchange stationary phases contained in the first and second columns at the initial pH; and h) repeating steps a) to g) as necessary to separate all of the molecular species of interest.

Two Hydrophilic Columns pH Gradient Plus One Component at Isocratic Concentration (Configuration B)

In yet another embodiment of the invention there is provided a method or system for chromatographically separating charged molecules having different isoelectric points, comprising:

a computer comprising a CPU, dynamic memory, and static memory and software which controls the operation of a multi-pump LC separation system; and at least two independent fluid delivery channels A and B, having fluid delivery rates which are independently controlled by software running on a computer; and a reservoir, $R_A$ containing an acidic buffer selected from the group consisting of the class of acidic pISep buffers, and an IC; and a reservoir, $R_B$, containing a basic buffer selected from the group consisting of the class of basic pISep buffers, and an IC; a pump A that controls the efflux of acidic buffer from reservoir $R_A$ and a pump B that controls the efflux of basic buffer from reservoir $R_B$; and at least two columns containing stationary phases selected from the group of stationary phases consisting of strong anionic exchange stationary phases, strong cationic exchange stationary phases, weak anionic exchange stationary phases, and weak cationic exchange stationary phases; and software configured such that if there are two columns of stationary phases then the software directs and controls the LC to perform:

a combined external pH gradient LC method for separating charged molecules having different isoelectric points, comprising:

applying the charged molecules to be separated to either (i) an anion exchange stationary phase in a first column, which is followed by a cation exchange stationary phase in a second column connected in series or (ii) a cation exchange stationary phase in the first column, which is followed by an anion exchange stationary phase in the second column connected in series, such that in both configurations (i) and (ii) the stationary phases are perfused with an eluent comprising at least one buffering component and an IC at a predetermined initial pH, wherein each of the charged molecules to be separated fall into one of three charge classes: apparently negatively charged for those charged molecules that have apparent isoelectric points (pIs) below the initial pH when in contact with the anionic exchange stationary phase; apparently neutral for those charged molecules that fail to bind to either the anion exchange stationary phase or the cation exchange stationary phase at the initial pH; and apparently positively charged for those charged molecules that have apparent pIs above the initial pH when in contact with the cationic exchange stationary phase;

binding the charged molecules which are apparently negatively charged at the initial pH to the anion exchange stationary phase;

binding the charged molecules which are apparently positively charged at the initial pH to the cation exchange stationary phase;

collecting the charged molecules which fail to bind to either the cation exchange stationary phase or the anion exchange stationary phase at the initial pH;

disconnecting, as directed by software, the anion exchange stationary phase and the cation exchange stationary phase in (i) or (ii) from each other;

supplying to the anion exchange stationary phase an eluent with a time dependent decreasing pH starting at the initial pH formed from the continuous mixing of (iii) a solution at a predetermined acidic pH containing the at least one buffering component and an IC pumped out from reservoir $R_A$ with (iv) a solution at a predetermined alkaline pH containing the at least one buffering component and an IC pumped out from $R_B$, wherein the mixing proportions of the solutions from the $R_A$ and $R_B$ reservoirs vary to maintain an unretained pH gradient with an externally defined slope;

collecting the charged molecules, each of which consecutively elutes from the anion exchange stationary phase at its effective isoelectric point, until a predetermined final minimum pH is reached;

supplying to the cation exchange stationary phase an eluent with a time dependent increasing pH starting at the initial pH formed from the continuous mixing of (v) a solution at a predetermined acidic pH containing the at least one buffering component and an IC pumped out from reservoir $R_A$ with (vi) a solution at a predetermined alkaline pH containing the at least one buffering component and an IC pumped out from $R_B$, wherein the mixing proportions of the solutions from the $R_A$ and $R_B$ reservoirs vary to maintain an unretained pH gradient with an externally defined slope; and collecting the charged molecules, each of which consecutively elutes from the cation exchange stationary phase at its effective isoelectric point until a predetermined final maximum pH is reached.

One Hydrophilic Column, One Hydrophobic Column, Sequential Gradients

In still another embodiment of the invention, there is provided a method or system for chromatographically separating charged molecules having different isoelectric points, comprising:

a computer comprising a CPU, dynamic memory, and static memory and software which controls the operation of a multi-pump LC separation system; and at least four independent fluid delivery channels A, B, C, and D having fluid delivery rates which are independently controlled by software running on a computer; and a reservoir, $R_A$, containing an acidic buffer selected from the group consisting of the class of acidic pISep buffers, and an IC; and a reservoir, $R_B$, containing a basic buffer selected from the group consisting of the class of basic pISep buffers, and an IC; a pump A that controls the efflux of acidic buffer from reservoir $R_A$ and a pump B that controls the efflux of basic buffer from reservoir $R_B$; and a reservoir, $R_C$ containing a solution comprising an IC that is a water miscible organic molecular species, hereafter referred to as a WMO, at a predetermined concentration; and a reservoir, $R_D$, containing a solution with a WMO at a concentration different from that in $R_C$; a pump C that controls the efflux of the solution from reservoir $R_C$ and a pump D that controls the efflux of the solution from reservoir $R_D$; and at least two columns containing stationary phases selected from the group of stationary phases consisting of strong anionic exchange stationary phases, strong cationic exchange stationary phases, weak anionic exchange stationary phases, weak cationic exchange stationary phases and hydrophobic stationary phases; and software configured such that if there are two columns of stationary phases, one of which is hydrophobic, then the software directs and controls the LC to perform:

a combined external pH gradient LC method for separating charged molecules having different isoelectric points, comprising:

applying and binding the charged molecules to be separated to a first column containing a cationic or anionic ion exchange stationary phase perfused with an eluent comprising at least one buffering component and an IC at a predetermined initial pH at which the ion exchange stationary phase has a charge opposite that of the charged molecules;

connecting in series after the first column a second column containing a hydrophobic stationary phase to the stationary phase contained in the first column and equilibrating the stationary phases contained in the first and second columns at the initial pH;

supplying to the ion exchange stationary phase contained in the first column an eluent with a variable pH starting at the initial pH formed from the continuous mixing of (i) a solution with a predetermined acidic pH containing the at least one buffering component and an IC pumped out from $R_A$ with (ii) a solution at a predetermined alkaline pH containing the at least one buffering component and an IC pumped out from reservoir $R_B$, wherein the mixing proportions of the solutions from the first and second reservoirs vary to maintain an unretained pH gradient with an externally defined slope;

a) eluting the charged molecules, each of which consecutively elutes from the ion exchange stationary phase contained in the first column at its effective isoelectric point until a predetermined final pH is reached;

b) directing for secondary separation the resulting effluent containing the consecutively eluted charged molecules from the first column into the hydrophobic stationary phase contained in the second column and;

c) binding the consecutively eluted charged molecules from the first column to the hydrophobic stationary phase contained in the second column until the predetermined final pH is reached;

d) disconnecting, as directed by software, the first column from the second column;

supplying to the hydrophobic stationary phase contained in the second column an eluent with a variable concentration of a WMO starting at an initial concentration of a WMO formed from the continuous mixing of (i) a solution with WMO at a particular concentration pumped out from reservoir $R_C$ with (ii) a solution containing a WMO at a concentration different from that in reservoir $R_C$ pumped out from reservoir $R_D$, wherein the mixing proportions of the solutions from the $R_C$ and $R_D$ reservoirs vary to maintain a gradient in the concentration of WMO with an externally defined slope; and e) collecting the molecules wherein each of the molecules consecutively elutes from the hydrophobic stationary phase contained in the second column according to the molecule's variation in hydrophobic binding free energy until a second predetermined final concentration of WMO is reached; and f) repeating steps a) to e) as necessary to separate all of the molecular species of interest.

Two Hydrophilic Columns: Anionic (or Cationic) First and One Hydrophobic, Sequential Gradients In yet another embodiment of the invention there is provided a method or system for chromatographically separating charged molecules having different isoelectric points, comprising:

a computer comprising a CPU, dynamic memory, and static memory and software which controls the operation of a multi-pump LC separation system; and at least four independent fluid delivery channels A, B, C, and D having fluid delivery rates which are independently controlled by software running on a computer; a reservoir, $R_A$ containing an acidic buffer selected from the group consisting of the class of acidic pISep buffers, and an IC; a reservoir, $R_B$, containing a basic buffer selected from the group consisting of the class of basic pISep buffers, and an IC; a pump A that controls the efflux of acidic buffer from reservoir $R_A$ and a pump B that controls the efflux of basic buffer from reservoir $R_B$; a reservoir, $R_C$ containing a solution with an IC that is a water miscible organic molecular species at a predetermined concentration; and a reservoir, $R_D$, containing a solution with a WMO at a concentration different from that in $R_C$; a pump C that controls the efflux of the solution from reservoir $R_C$ and a pump D that controls the efflux of the solution from reservoir $R_D$; and at least two columns containing stationary phases selected from the group of stationary phases consisting of strong anionic exchange stationary phases, strong cationic exchange stationary phases, weak anionic exchange stationary phases, and weak cationic exchange stationary phases; and a third column containing a hydrophobic stationary phase; and software configured such that if there are two columns of stationary phases, one of which is hydrophobic, then the software directs and controls the LC to perform:

a combined external pH gradient LC method for separating charged molecules having different isoelectric points, comprising:

applying the charged molecules to be separated to an anion (cation exchange stationary phase) exchange stationary phase in a first column, which is followed by a cation (anion exchange stationary phase) exchange stationary phase in a second column connected in series to the first column which is followed by a third column containing a hydrophobic stationary phase connected in series to the second column, such that the stationary phases are perfused with an eluent comprising at least one buffering component and an IC at a predetermined initial pH, wherein each of the charged molecules to be separated fall into one of three charge classes: apparently negatively charged for those charged molecules that have apparent isoelectric points (pIs) below the initial pH when in contact with the anionic exchange stationary phase; apparently neutral for those charged molecules that fail to bind to either the anion exchange stationary phase or the cation exchange stationary phase at the initial pH; and apparently positively charged for those charged molecules that have apparent pIs above the initial pH when in contact with the cationic exchange stationary phase; and a) binding the charged molecules which are apparently negatively charged at the initial pH to the anion stationary phase;

b) binding the charged molecules which are apparently positively charged at the initial pH to the cation stationary phase;

c) directing the apparently neutral molecules which fail to bind to either the cation exchange stationary phase or the anion exchange stationary phase at the initial pH onto the third column containing a hydrophobic stationary phase to which they will bind;

d) disconnecting, as directed by software, the anion (cation) exchange column followed by the cation (anion) exchange column from the hydrophobic stationary phase;

supplying to the hydrophobic stationary phase an eluent with a time dependent increasing hydrophobicity formed from the continuous mixing of (iii) a solution containing a predetermined concentration of a WMO pumped out from $R_C$ with (iv) a solution with a different predetermined concentration of a WMO pumped out from $R_d$, wherein the mixing proportions of the solutions from the $R_C$ and $R_d$ reservoirs vary to maintain a gradient with an externally defined slope in WMO concentration;

collecting the separated molecular fractions as they elute from the hydrophobic column according to their hydrophobicity;

disconnecting, as directed by software, the anion (cation exchange stationary phase) exchange stationary phase followed by the cation (anion stationary phase) exchange stationary phase from each other;

connecting in a series, as directed by software, the anion (cation stationary phase) exchange stationary phase followed by the hydrophobic stationary phase to each other;

supplying to the anion (cation stationary phase) exchange stationary phase an eluent with a time dependent decreasing (increasing for cation stationary phase) pH starting at the initial pH formed from the continuous mixing of (iii) a solution at a predetermined acidic pH containing the at least one buffering component and an IC pumped out from $R_A$ with (iv) a solution at a predetermined alkaline pH containing the at least one buffering component and an IC pumped out from $R_B$, wherein the mixing proportions of the solutions from the first and second two reservoirs vary to maintain an unretained pH gradient with an externally defined slope;

directing the charged molecules, each of which consecutively elutes from the anion (cation stationary phase) exchange stationary phase at its effective isoelectric point, onto the column containing the hydrophobic stationary phase where they will bind; until a predetermined final minimum (or maximum for cation stationary phase) pH is reached;

disconnecting, as directed by software, the anion (cation stationary phase) exchange column and the hydrophobic column from each other;

supplying to the hydrophobic stationary phase an eluent with a time dependent increasing hydrophobicity formed from the continuous mixing of (iii) a solution with a predetermined concentration of a WMO pumped out from reservoir $R_C$ with (iv) a solution containing different predetermined concentration of a WMO pumped out from reservoir $R_d$, wherein the mixing proportions of the solutions from the $R_C$ and $R_d$ reservoirs vary to maintain an gradient with an externally defined slope in WMO concentration;

collecting the separated molecular fractions as they elute from the hydrophobic column according to their hydrophobicity;

connecting, as directed by software, the cation (anion stationary phase) exchange stationary phase and the hydrophobic stationary phase to each other;

supplying to the cation (anion stationary phase) exchange stationary phase an eluent with a time dependent increasing (decreasing for anion stationary phase) pH starting at the initial pH formed from the continuous mixing of (v) a solution at a predetermined acidic pH containing the at least one buffering component and an IC pumped out from $R_A$ with (vi) a solution at a predetermined alkaline pH containing the at least one buffering component and an IC pumped out from $R_B$, wherein the mixing proportions of the solutions from the $R_A$ and $R_B$ reservoirs vary to maintain an unretained pH gradient with an externally defined slope;

directing the charged molecules, each of which consecutively elutes from the cation (anion stationary phase) exchange stationary phase at its effective isoelectric point, onto the column containing a hydrophobic stationary phase where they will bind; until a predetermined final maximum (maximum for cation stationary phase) pH is reached;

disconnecting, as directed by software, the cation (anion stationary phase) exchange stationary phase and the hydrophobic stationary phase from each other;

supplying to the hydrophobic stationary phase an eluent with a time dependent increasing hydrophobicity formed from the continuous mixing of (iii) a solution with a predetermined concentration of a WMO pumped out from reservoir $R_C$ with (iv) a solution containing a different predetermined concentration of a WMO pumped out from reservoir $R_d$, wherein the mixing proportions of the solutions from the $R_C$ and $R_d$ reservoirs vary to maintain an gradient with an externally defined slope in WMO concentration; and collecting the separated molecular fractions as they elute from the hydrophobic column according to their hydrophobicity.

Manifold Equations for the Creation of Independent Simultaneous Gradients

An equation family that specifies the relationship between the % acidic pISep buffer (A %) in the eluent stream and the pH in the presence of an additive E is: A %=$a_n*E^n+a_{n-1}*E^{n-1}+ \ldots +a_1*E+a_0$, where $a_n$ through $a_0$ are each distinct functions of pH of the form:

$k_{a_n,p}*pH^{p_m}+k_{a_n p_m-1}*pH^{p_m-1}+ \ldots +k_{a_n}, 1 \leq m \leq n, p \geq 0$, the k's being fitting constants. These k's are determined by fitting the curve of each coefficient $a_n \ldots a_0$ versus pH at constant E. This allows the formation of independent simultaneous gradients in the pH and the additive on the same column(s). It is possible to generalize this to two or more additives, E, F, G and so on by calculating a multi dimensional manifold. An example for two additives, with concentrations E and F, plus pH would be as follows: A %=$a*E^5+b*E^4+c*E^3+d*E^2+e*E+f$, where a through f are each distinct functions of F and pH of the form: a(F,pH), b(F,pH), etc. By creating a series of manifolds each with a different constant concentration of F, the functional dependence of each of the a(F,pH), b(F,pH) on F and pH can be calculated for each manifold. Because there are a family of manifolds each calculated at a distinct value of F each of the coefficients of the powers of E, are not constants but functions of F of the form: $a_{5,F}*F^5+a_{4,F}*F^4+a_{3,F}*F^3+a_{2,F}*F^2+a_{1,F}*F+a_{0,F}$, $b_{5,F}*F^5+b_{4,F}*F^4+b_{3,F}*F^3+b_{2,F}*F^2+b_{1,F}*F+b_{0,F}$, . . . $f_{5,F}*F^5+f_{4,F}*F^4+f_{3,F}*F^3+f_{2,F}*F^2+f_{1,F}*F+f_{0,F}$ as determined by plotting each of the a, b . . . e,f versus F at constant pH. Likewise, each of the coefficients of the powers of F would be fit to a distinct polynomial in pH alone. It should be understood that other sets of equations may be appropriate for any particular set of n additives: A %=$F(E_1, E_1, \ldots E_{n-1}, E_n, pH)$ with the mathematical forms of the equations not limited to polynomials in the concentrations of the additives or pH. It then it may be possible to control the formation of n independent gradients by using such an equation set to control flow from each of the $2^n$ reservoirs. An example of this would be a single additive with a competitive buffering capacity, as perhaps might be expected from a basic solute like tetraethylammonium chloride( ), such that: A %=$a(pH)*E_{TEA}^{b(pH)}$.

One Hydrophilic Column, Simultaneous Independent Gradients

In still another embodiment of the invention, there is provided a method or system for chromatographically separating charged molecules having different isoelectric points, comprising:

a computer comprising a CPU, dynamic memory, and static memory and software which controls the operation of a multi-pump LC separation system; and at least four independent fluid delivery channels A, B, C, and D having fluid delivery rates which are independently controlled by software running on a computer; a reservoir, $R_A$ containing an acidic buffer selected from the group consisting of the class of acidic pISep buffers; a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; a reservoir, $R_C$ containing an acidic buffer selected from the group consisting of the class of acidic pISep buffers, and an IC at a maximum concentration; and a reservoir, $R_D$, containing a basic buffer selected from the group consisting of the class of basic pISep buffers, and the IC at the maximum concentration; a pump C that controls the efflux of acidic buffer plus IC from reservoir $R_C$ and a pump D that controls the efflux of basic buffer plus IC from reservoir $R_D$; and the proportion of eluent pumped from $R_A$ vs. the proportion pumped from $R_C$ to create an acidic eluent mixture is determined by the software with the concentration of IC called for by the gradient in IC is programmed into software by the user and the same proportion of eluent pumped from $R_B$ vs. the proportion pumped from $R_D$ to create the same concentration of IC called for by the gradient in IC is programmed into the software by the user; and the proportion of the total eluent stream consisting of the acidic mixture vs. the proportion of the eluent stream consisting of the basic mixture is determined by the software by utilizing the manifold equations that define, at any concentration of IC up to the selected maximum, what should be the proportion of acidic buffer containing the gradient determined concentration of IC programmed into software by the user and what should be the proportion of basic buffer containing the gradient determined concentration of IC programmed into software by the user so as to produce the pH determined by the pH gradient programmed into software by the user and; at least one column containing stationary phases selected from the group of stationary phases consisting of strong anionic exchange stationary phases, strong cationic exchange stationary phases, weak anionic exchange stationary phases, and weak cationic exchange stationary phases; and software configured such that if there is one column of stationary phases, then the software directs and controls the LC to perform:

a combined external pH gradient LC method for separating charged molecules having different isoelectric points, comprising:

applying and binding the charged molecules to be separated to a column containing a cationic or anionic ion exchange stationary phase perfused with an eluent comprising at least one buffering component and an IC at a predetermined initial pH and a predetermined initial concentration of IC wherein the ion exchange stationary phase has a charge opposite that of the charged molecules;

supplying to the ion exchange stationary phase contained in the column an eluent with a variable pH and an independent variable IC concentration starting at the initial pH and the initial IC concentration as determined by the software by utilizing the manifold equations that define, at any concentration of IC up to the selected maximum, what should be the proportion of acidic buffer containing the gradient determined concentration of IC programmed into software by the user and what should be the proportion of basic buffer containing the gradient determined concentration of IC programmed into software by the user so as to produce the pH determined by the pH gradient programmed into software by the user in order to maintain an unretained pH gradient with an externally defined slope and an independent and simultaneous unretained gradient in the concentration of IC:

a) eluting the charged molecules, each of which consecutively elutes from the ion exchange stationary phase contained in the column at its effective isoelectric point until a predetermined final pH and a predetermined concentration of IC is reached; and b) collecting the charged molecules wherein each of the molecules consecutively elutes from the ion exchange stationary phase contained in the column at its effective isoelectric point until the predetermined final pH and the predetermined final IC concentration is reached: and c) repeating steps a)-b) as necessary to separate all of the molecular species of interest.

Two Hydrophilic Columns, Simultaneous Independent Gradients

In still another embodiment of the invention, there is provided a method or system for chromatographically separating charged molecules having different isoelectric points, comprising:

a computer comprising a CPU, dynamic memory, and static memory and software which controls the operation of a multi-pump LC separation system; and at least four independent fluid delivery channels A, B, C, and D having fluid delivery rates which are independently controlled by software running on a computer; a reservoir, $R_A$ containing an acidic buffer selected from the group consisting of the class of acidic pISep buffers; a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; a reservoir, $R_C$, containing an acidic buffer selected from the group consisting of the class of acidic pISep buffers, and an IC at a maximum concentration; and a reservoir, $R_D$, containing a basic buffer selected from the group consisting of the class of basic pISep buffers, and the IC at the maximum concentration; a pump C that controls the efflux of acidic buffer plus IC from reservoir $R_C$ and a pump D that controls the efflux of basic buffer plus IC from reservoir $R_D$; and the proportion of eluent pumped from $R_A$ vs. the proportion pumped from $R_C$ to created an acidic eluent mixture is determined in the software with the concentration of IC called for by the gradient in IC is programmed into the software by the user and the same proportion of eluent pumped from $R_B$ vs. the proportion pumped from $R_D$ to create the same concentration of IC called for by the gradient in IC is programmed into the software by the user; and the proportion of the total eluent stream consisting of the acidic mixture vs. the proportion of the eluent stream consisting of the basic mixture is determined by the software by utilizing the manifold equations that define, at any concentration of IC up to the selected maximum, what should be the proportion of acidic buffer containing the gradient determined concentration of IC programmed into software by the user and what should be the proportion of basic buffer containing the gradient determined concentration of IC programmed into software by the user so as to produce the pH determined by the pH gradient programmed into software by the user and; at least one column containing stationary phases selected from the group of stationary phases consisting of strong anionic exchange stationary phases, strong cationic exchange stationary phases, weak anionic exchange stationary phases, and weak cationic exchange stationary phases; and software configured such that if there are two columns of stationary phases, then software directs and controls:

a combined external pH gradient LC method for separating charged molecules having different isoelectric points, comprising:

applying and binding the charged molecules to be separated to a first column containing a cationic or anionic ion exchange stationary phase perfused with an eluent comprising at least one buffering component and an IC at a predetermined initial pH and a predetermined initial concentration of IC wherein the ion exchange stationary phase has a charge opposite that of the charged molecules;

connecting in series after the first column containing a cationic or anionic ion exchange stationary phase a second column containing a cationic or anionic ion exchange stationary phase of charge opposite to the first and equilibrating the stationary phases contained in the first and second columns at the initial pH;

supplying to the ion exchange stationary phase contained in the first column an eluent with a variable pH and an independent variable IC concentration starting at the initial pH and an initial IC concentration as determined by the software by utilizing the manifold equations that define, at any concentration of IC up to the selected maximum, what should be the proportion of acidic buffer containing the gradient determined concentration of IC programmed into software by the user and what should be the proportion of basic buffer containing the gradient determined concentration of IC programmed into software by the user so as to produce the pH determined by the pH gradient programmed into software by the user in order to maintain an unretained pH gradient with an externally defined slope and an independent and simultaneous unretained gradient in the concentration of IC;

a) eluting the charged molecules, each of which consecutively elutes from the ion exchange stationary phase contained in the first column at its effective isoelectric point until a predetermined final pH and a predetermined concentration of IC is reached;

b) directing for secondary separation the resulting effluent containing the consecutively eluted charged molecules from the first column into the ion exchange stationary phase contained in the second column and;

c) binding the charged molecules that are oppositely charged to the ion exchange stationary phase contained in the second column until the predetermined final pH and the predetermined concentration of IC is reached is reached;

d) disconnecting, as directed by software, the first column from the second column;

e) reversing the pH gradient perfusing the ion exchange stationary phase contained in the second column to develop to a second predetermined final pH from a second predetermined initial pH and simultaneously developing a second independent gradient to a predetermined final IC concentration from a second predetermined initial IC concentration; and f) collecting the charged molecules, wherein each of the molecules consecutively elutes from the ion exchange stationary phase contained in the second column at its effective isoelectric point until the second predetermined final pH and the second predetermined final IC concentration is reached;

g) optionally reconnecting by direction of software in series after the first column a second column containing an ion exchange stationary phase of the opposite charge to the stationary phase contained in the first column and equilibrating the ion exchange stationary phases contained in the first and second columns at the initial pH and the initial IC concentration; and h) repeating steps a) to g) as necessary to separate all of the molecular species of interest.

One Hydrophilic Column, One Hydrophobic Column, Simultaneous Gradients

In still another embodiment of the invention, there is provided a method or system for chromatographically separating charged molecules having different isoelectric points, comprising:

a computer comprising a CPU, dynamic memory, and static memory and software that controls the operation of a multi-pump LC separation system; and at least four independent fluid delivery channels A, B, C, and D having fluid delivery rates which are independently controlled by software running on a computer; a reservoir, $R_A$ containing an acidic buffer selected from the group consisting of the class of acidic pISep buffers and a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; and a reservoir, $R_C$, containing an acidic buffer selected from the group consisting of the class of acidic pISep buffers, and an IC; a reservoir, $R_D$, containing a basic buffer selected from the group consisting of the class of basic pISep buffers, and an IC; a pump C that controls the efflux of acidic buffer plus IC from reservoir $R_C$ and a pump D that controls the efflux of basic buffer plus IC from reservoir $R_D$; and at least two columns containing stationary phases selected from the group of stationary phases consisting of strong anionic exchange stationary phases, strong cationic exchange stationary phases, weak anionic exchange stationary phases, weak cationic exchange stationary phases and hydrophobic stationary phases; and software configured such that if there are two columns of stationary phases, one of which is hydrophobic, then the software directs and controls:

a combined external pH gradient LC method for separating charged molecules having different isoelectric points, comprising:

applying and binding the charged molecules to be separated to a first column containing a cationic or anionic ion exchange stationary phase perfused with an eluent comprising at least one buffering component and an IC at a predetermined initial pH and a predetermined initial concentration of IC wherein the ion exchange stationary phase has a charge opposite that of the charged molecules;

connecting in series after the first column containing a cationic or anionic ion exchange stationary phase, a second column containing a hydrophobic stationary phase and equilibrating the stationary phases contained in the first and second columns at the initial pH;

supplying to the ion exchange stationary phase contained in the first column an eluent with a variable pH starting at the initial pH and an initial IC concentration formed from the continuous mixing of (i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC;

a) eluting the charged molecules, each of which consecutively elutes from the ion exchange stationary phase contained in the first column at its effective isoelectric point until a predetermined final pH and final IC concentration is reached;

b) directing for secondary separation the resulting effluent containing the consecutively eluted charged molecules from the first column into the hydrophobic stationary phase contained in the second column;

c) binding the consecutively eluted charged molecules from the first column that are sufficiently hydrophobic to the hydrophobic stationary phase contained in the second column until the predetermined final pH is reached;

d) collecting the separated molecular fractions not bound to the second column;

e) disconnecting, as directed by software, the first column from the second column;

f) supplying to the hydrophobic stationary phase contained in the second column an eluent with a variable concentration of a WMO starting at an initial concentration of a WMO formed from the continuous mixing of (i) a solution with predetermined pH containing the at least one buffering component and a WMO at a particular concentration pumped out from a first reservoir with (ii) a solution at a predetermined pH containing the at least one buffering component and a WMO at a concentration different from that in the first reservoir pumped out from a second reservoir, wherein the mixing proportions of the solutions from the first and second reservoirs vary to maintain a gradient in the concentration of WMO with an externally defined slope; and g) collecting the charged molecules, wherein each of the charged molecules consecutively elutes from the hydrophobic stationary phase contained in the second column according to the molecule's variation in hydrophobic binding free energy until a second predetermined final concentration of WMO is reached; and h) repeating steps a)-g) as necessary to separate all of the molecular species of interest.

Two Hydrophilic Columns Anionic and Cationic and One Hydrophobic, Simultaneous Dual Gradients In yet another embodiment of the invention there is provided a method or system for chromatographically separating charged molecules having different isoelectric points, comprising:

a computer comprising a CPU, dynamic memory, and static memory and software that controls the operation of a multi-pump LC separation system; and at least four independent fluid delivery channels A, B, C, and D having fluid delivery rates that are independently controlled by software running on a computer; a reservoir, $R_A$ containing an acidic buffer selected from the group consisting of the class of acidic pISep buffers; a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; a reservoir, $R_C$ containing an acidic buffer selected from the group consisting of the class of acidic pISep buffers, and an IC; a reservoir, $R_D$, containing a basic buffer selected from the group consisting of the class of basic pISep buffers, and an IC; a pump C that controls the efflux of acidic buffer plus IC from reservoir $R_C$ and a pump D that controls the efflux of basic buffer plus IC from reservoir $R_D$; and at least three columns containing stationary phases selected from the group of stationary phases consisting of strong anionic exchange stationary phases, strong cationic exchange stationary phases, weak anionic exchange stationary phases, weak cationic exchange stationary phases and hydrophobic stationary phases; and software configured such that if there are two columns of hydrophilic stationary phases and one column of hydrophobic stationary phase then software directs and controls:

a combined external pH gradient LC method for separating charged molecules having different isoelectric points, comprising:

applying and binding the charged molecules to be separated to a first column containing a cationic or anionic ion exchange stationary phase perfused with an eluent comprising at least one buffering component and an IC at a predetermined initial pH and a predetermined initial concentration of IC wherein the ion exchange stationary phase has a charge opposite that of the charged molecules;

connecting in series after the first column containing a cationic or anionic ion exchange stationary phase a second column containing a cationic or anionic ion exchange stationary phase of charge opposite to the first and equilibrating the stationary phases contained in the first and second columns at the initial pH;

connecting in series after the second column containing a cationic or anionic ion exchange stationary phase a third column containing a hydrophobic stationary phase and equilibrating the stationary phases contained in the first, second and third columns at the initial pH;

supplying to the ion exchange stationary phase contained in the first column an eluent with a variable pH starting at the initial pH and an initial IC concentration formed from the continuous mixing of (i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC; and a) binding the charged molecules which are apparently negatively charged at the initial pH to an anion exchange stationary phase;

b) binding the charged molecules which are apparently positively charged at the initial pH to an cation exchange stationary phase;

c) collecting the apparently neutral molecules which fail to bind to either the cation exchange stationary phase or the anion exchange stationary phase at the initial pH;

d) directing the fraction containing the apparently neutral molecules onto the third column containing a hydrophobic stationary phase where they will bind;

disconnecting, as directed by software, the anion exchange stationary phase and the cation exchange stationary phase from the hydrophobic stationary phase;

supplying to the hydrophobic stationary phase an eluent with a time dependent increasing hydrophobicity formed from the continuous mixing of (iii) a solution at a predetermined pH and at a predetermined concentration of a WMO pumped out from $R_C$ with (iv) a solution at a predetermined pH at a different predetermined concentration of a WMO pumped out from $R_d$, wherein the mixing proportions of the solutions from the first and second two reservoirs vary to maintain an unretained gradient with an externally defined slope in WMO concentration;

collecting the separated molecular fractions as they elute from the hydrophobic column;

disconnecting, as directed by software, the anion exchange stationary phase and the cation exchange stationary phase from each other;

connecting, as directed by software, the anion exchange stationary phase and the hydrophobic stationary phase to each other;

supplying to the anion exchange stationary phase contained in the first column an eluent with a variable pH starting at the initial pH and an initial IC concentration formed from the continuous mixing of (i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC; and directing the charged molecules, each of which consecutively elutes from the anion exchange stationary phase at its effective isoelectric point, onto the column containing a hydrophobic stationary phase where they will bind until a predetermined final minimum pH and predetermined final concentration of WMO is reached;

disconnecting, as directed by software, the anion exchange stationary phase and the hydrophobic stationary phase from each other;

supplying to the hydrophobic stationary phase an eluent with a time dependent increasing hydrophobicity formed from the continuous mixing of (iii) a solution at a predetermined pH and at a predetermined concentration of a WMO pumped out from $R_C$ with (iv) a solution at a predetermined pH at a different predetermined concentration of a WMO pumped out from $R_d$, wherein the mixing proportions of the solutions from the first and second two reservoirs vary to maintain an unretained gradient with an externally defined slope in WMO concentration;

collecting the separated molecular fractions as they elute from the hydrophobic column;

connecting, as directed by software, the cation exchange stationary phase and the hydrophobic stationary phase to each other;

supplying to the cation exchange stationary phase contained in the first column an eluent with a variable pH starting at the initial pH and an initial IC concentration formed from the continuous mixing of (i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC; and directing the charged molecules, each of which consecutively elutes from the cation exchange stationary phase at its effective isoelectric point, onto the column containing a hydrophobic stationary phase where they will bind; until a predetermined final maximum pH is reached;

disconnecting, as directed by software, the cation exchange stationary phase and the hydrophobic stationary phase from each other;

supplying to the hydrophobic stationary phase an eluent with a time dependent increasing hydrophobicity formed from the continuous mixing of (iii) a solution at a predetermined pH and at a predetermined concentration of a WMO pumped out from $R_C$ with (iv) a solution at a predetermined pH at a different predetermined concentration of a WMO pumped out from $R_d$, wherein the mixing proportions of the solutions from the first and second two reservoirs vary to maintain an unretained gradient with an externally defined slope in WMO concentration; and collecting the separated molecular fractions as they elute from the hydrophobic column.

One Mixed Mode Column, Simultaneous Gradients

In still another embodiment of the invention, there is provided a method or system for chromatographically separating charged molecules having different isoelectric points, comprising:

a computer comprising a CPU, dynamic memory, and static memory and software that controls the operation of a multi-pump LC separation system; and at least four independent fluid delivery channels A, B, C, and D having fluid delivery rates that are independently controlled by software running on a computer; a reservoir, $R_A$ containing an acidic buffer selected from the group consisting of the class of acidic pISep buffers; a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; and a reservoir, $R_C$ containing an acidic buffer selected from the group consisting of the class of acidic pISep buffers, and an IC; and a reservoir, $R_D$, containing a basic buffer selected from the group consisting of the class of basic pISep buffers, and an IC; a pump C that controls the efflux of acidic buffer plus IC from reservoir $R_C$ and a pump D that controls the efflux of basic buffer plus IC from reservoir $R_D$; and a column containing a mixture of both hydrophobic stationary phases and either cationic or anionic stationary phases; and software configured such that if there is one column of stationary phases, then the software directs and controls:

a combined external pH gradient LC method for separating charged molecules having different isoelectric points, comprising:

applying and binding the charged molecules to be separated to a column containing a cationic or anionic mixed mode stationary phase and a hydrophobic stationary phase perfused with an eluent comprising at least one buffering component and an IC at a predetermined initial pH and a predetermined initial concentration of IC wherein the charged molecules are bound to the stationary phase because they have a charge opposite that of the absorbent or because the hydrophobic forces between the charged molecules and the stationary phase are sufficient to immobilize the charged molecules on the stationary phase or both;

supplying to the mixed mode stationary phase contained in the column an eluent with a variable pH starting at the initial pH and an initial IC concentration formed from the continuous mixing of (i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC;

a) eluting the charged molecules, each of which consecutively elutes from the mixed mode stationary phase contained in the column at its effective isoelectric point until a predetermined final pH and a predetermined concentration of IC is reached;

b) collecting the charged molecules wherein each of the molecules consecutively elutes from the ion exchange stationary phase contained in the column at its effective isoelectric point until the predetermined final pH and the predetermined final IC concentration is reached; and c) repeating steps a)-b) as deemed necessary to separate all of the molecular species of interest.

One Hydrophilic Column, Simultaneous Generalized Dual Gradients

In still another embodiment of the invention, there is provided a method or system for chromatographically separating charged molecules having different isoelectric points, comprising:

a computer comprising a CPU, dynamic memory, and static memory and software that controls the operation of a multi-pump LC separation system; and at least four independent fluid delivery channels A, B, C, and D having fluid delivery rates that are independently controlled by software running on a computer; a reservoir, $R_A$ containing a solution at a buffered pH and a reservoir, $R_B$, containing a solution of a first IC at a buffered pH; a pump A that controls the efflux of solution from reservoir $R_A$ and a pump B that controls the efflux of solution from reservoir $R_B$; and a reservoir, $R_C$ containing a solution of a second IC at a buffered pH; and a reservoir, $R_D$, containing a solution of a first IC and a second IC at a buffered pH; a pump C that controls the efflux of efflux of solution from reservoir $R_C$ and a pump D that controls the efflux of solution from reservoir $R_D$; and at least one column containing stationary phases selected from the group of stationary phases consisting of strong anionic exchange stationary phases, strong cationic exchange stationary phases, weak anionic exchange stationary phases, and weak cationic exchange stationary phases; and software configured such that if there is one column of stationary phases, then the software directs and controls:

a combined external dual gradient LC method for separating charged molecules having different isoelectric points, comprising:

applying and binding the charged molecules to be separated to a column containing a cationic or anionic ion exchange stationary phase perfused with an eluent comprising at least one buffering component, a first IC and a second IC at a predetermined initial pH and a predetermined initial concentration of the first IC and a predetermined initial concentration of the second IC wherein the ion exchange stationary phase has a charge opposite that of the charged molecules;

supplying to the ion exchange stationary phase contained in the column an eluent with a fixed pH starting at the initial concentration of the first IC and the initial concentration of the second IC formed from the continuous mixing of (i) a solution with the at least one buffering component pumped out from $R_A$ and a solution with predetermined concentration of the first IC containing the at least one buffering component pumped out from $R_B$, a first pair of reservoirs, and mixed so as to produce a predetermined concentration of the first IC; and (ii) a solution containing the at least one buffering component and a second IC pumped out from $R_C$ and a solution containing the at least one buffering component and both a first IC and a second IC pumped out from $R_D$, a second pair of reservoirs, and mixed so as to produce the predetermined concentration of the first IC and a predetermined concentration of the second IC, wherein the mixing proportions of the solutions from the first and second pairs of reservoirs vary to maintain independent and simultaneous unretained gradients in the concentration of the first IC and the second IC each gradient with its own externally defined slope;

a) eluting the charged molecules, each of which consecutively elutes from the ion exchange stationary phase contained in the column at its effective isoelectric point until a predetermined final predetermined concentration of the first IC and a predetermined concentration of the second IC is reached; and b) collecting the charged molecules wherein each of the molecules consecutively elutes from the ion exchange stationary phase contained in the column at its effective isoelectric point until the predetermined final concentration of the first IC is reached; and the predetermined final concentration of the second IC is reached; and c) repeating steps a)-b) as deemed necessary to separate all of the molecular species of interest.

One Hydrophobic Column, Simultaneous Generalized Dual Gradients

In still another embodiment of the invention, there is provided a method or system for chromatographically separating molecules having different effective isohydrophobicity points, EIH, comprising:

a computer comprising a CPU, dynamic memory, and static memory and software that controls the operation of a multi-pump LC separation system; and at least four independent fluid delivery channels, A, B, C, and D having fluid delivery rates that are independently controlled by software running on a computer; and a reservoir, $R_A$, containing a solution at a buffered pH and a reservoir, $R_B$, containing a solution of a first IC at a buffered pH; a pump A that controls the efflux of solution from reservoir $R_A$ and a pump B that controls the efflux of solution from reservoir $R_B$; and a reservoir, $R_C$, containing a solution of a second IC at a buffered pH; and a reservoir, $R_D$, containing a solution of a first IC and a second IC at a buffered pH; a pump C that controls the efflux of efflux of solution from reservoir $R_C$ and a pump D that controls the efflux of solution from reservoir $R_D$; and a column containing stationary phases chosen from a group of stationary phases consisting of hydrophobic stationary phases; and software configured such that the software directs and controls:

a combined external dual gradient LC method for separating molecules having different effective EIH points, comprising:

applying and binding the molecules to be separated to a column containing a hydrophobic stationary phase perfused with an eluent comprising at least one buffering component, a first IC and a second IC at a predetermined initial pH and a predetermined initial concentration of the first IC and a predetermined initial concentration of the second IC wherein the hydrophobic stationary phase is able to immobilize and bind all of the molecules to be separated;

supplying to the hydrophobic stationary phase contained in the column an eluent with a fixed pH starting at the initial concentration of the first IC and the initial concentration of the second IC formed from the continuous mixing of (i) a solution with the at least one buffering component pumped out from $R_A$ and a solution with predetermined concentration of the first IC containing the at least one buffering component pumped out from $R_B$, a first pair of reservoirs, and mixed so as to produce a predetermined concentration of the first IC; and (ii) a solution containing the at least one buffering component and a second IC pumped out from $R_C$ and a solution containing the at least one buffering component and both a first IC and a second IC pumped out from $R_D$, a second pair of reservoirs, and mixed so as to produce the predetermined concentration of the first IC and a predetermined concentration of the second IC, wherein the mixing proportions of the solutions from the first and second pairs of reservoirs vary to maintain independent and simultaneous unretained gradients in the concentration of the first IC and the second IC each gradient with its own externally defined slope;

a) eluting the molecules, each of which consecutively elutes from the hydrophobic stationary phase contained in the column at its EIH until a predetermined final predetermined concentration of the first IC and a predetermined concentration of the second IC is reached; and b) collecting the molecules wherein each of the molecules consecutively elutes from the ion exchange stationary phase contained in the column at its EIH until the predetermined final concentration of the first IC is reached and the predetermined final concentration of the second IC is reached; and c) repeating steps a)-b) as deemed necessary to separate all of the molecular species of interest.

One Hydrophilic Column, Simultaneous Generalized Multi-Component Gradients Scaled Arithmetically In still another embodiment of the invention, there is provided a method or system for chromatographically separating charged molecules having different isoelectric points, comprising:

a computer comprising a CPU, dynamic memory, static memory and software that controls the operation of an n gradient LC separation system, $n \geq 3$; and at least $2^n$ independent fluid delivery channels $A_1, A_2, \ldots A_{2^n}$, whose fluid delivery rates are independently controlled by software running on a computer; and a reservoir, $R_1$ containing a solution at a buffered pH and a reservoir, $R_2$, containing a solution of a first IC at a buffered pH; a pump $A_1$ that controls the efflux of solution from reservoir $R_1$ and a pump $A_2$ that controls the efflux of solution from reservoir $R_2$; and a reservoir, $R_3$ containing a solution of a second IC at a buffered pH; and a reservoir, $R_4$, containing a solution of a first IC and a second IC at a buffered pH; a pump $A_3$ that controls the efflux of efflux of solution from reservoir $R_3$ and a pump $A_4$ that controls the efflux of solution from reservoir $R_4$ and so on for a total of $R_2{}^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary $m^{th}$ subset of $2^{n-1}$ reservoirs not containing that $IC_m$ such that the distribution of the IC follows the following mathematical rules:

for a first component, $IC_1$, if j MOD 2=1, for all j $\ni 2^n \geq j \geq 1$, then $[IC_1]$ in $R_j = 0$ else $[IC_1]$ in $R_j$=a maximum of $[IC_1]$, $[IC_{1=max}]$, attainable for the particular separation being attempted; and each of the m components $\ni n \geq m > 1$, and for all k $\ni (2^n/2^{(m-1)}) \geq k \geq 1$, then if k MOD 2=1 then if $(k*2^{(m-1)}) \geq j \geq (k*2^{(m-1)} - (2^{(m-1)} - 1))$ then $R_j = 0$, else $[IC_m]$ in $R_j$=a maximum of $[IC_m]$, $[IC_{m=max}]$, set by the chromatographer for the particular separation being attempted;

and at least one column containing stationary phases chosen from a group of stationary phases consisting of strong anionic exchange stationary phases, strong cationic exchange stationary phases, weak anionic exchange stationary phases, and weak cationic exchange stationary phases; and software configured such that if there is one column of stationary phases, then software directs and controls:

a combined external n gradient LC method for separating charged molecules having different isoelectric points, comprising:

applying and binding the charged molecules to be separated to a column containing a cationic or anionic ion exchange stationary phase perfused with an eluent comprising at least one buffering component, a first IC, a second IC, up to and including an nth IC at a predetermined initial pH and a predetermined initial concentration of the first IC and a predetermined initial concentration of the second IC up to a predetermined initial concentration of the nth IC wherein the ion exchange stationary phase has a charge opposite that of the charged molecules;

supplying to the ion exchange stationary phase contained in the column an eluent with a fixed pH starting at the initial concentration of the first IC and the initial concentration of the second IC formed from the continuous mixing of (i) a solution with the at least one buffering component pumped out from $R_1$ and a solution with a maximum predetermined concentration of the first IC containing the at least one buffering component pumped out from $R_2$, a first pair of reservoirs, and mixed so as to produce a predetermined concentration of the first IC; and (ii) a solution containing the at least one buffering component and a predetermined maximum concentration of a second IC pumped out from $R_3$ and a solution containing the at least one buffering component and both a predetermined maximum concentration of a first IC and a predetermined maximum concentration of a second IC pumped out from $R_4$, a second pair of reservoirs, and mixed so as to produce the predetermined concentration of the first IC and a predetermined maximum concentration of the second IC, wherein the mixing proportions of the solutions from the first and second pairs of reservoirs vary to maintain independent and simultaneous unretained gradients in the concentration of the first IC and the second IC each gradient with its own externally defined slope when the efflux from the two pairs are mixed and so on up to n independent simultaneous gradients such that the mixing of the n IC follows the following mathematical rules:

for the $n^{th}$ component there is associated with any point in its gradient a target concentration, $[IC_{n,target}]$ such that $F_{v,n=max,target}=([IC_{n,target}]/[IC_{n=max}])*F_v$, where $F_v$ is total eluent flow, and $F_{v,n=max,target}$ is the total flow contributed by combining the flows of all the reservoirs containing $[IC_{n=max}]$ and $F_{v,n=0,target}=F_v-F_{v,n=max,target}$ is the total flow contributed by combining the flows of all the reservoirs containing $[IC_{n=0}]$; for the $(n-1)^{th}$ component there are four flows, two are combined to produce $F_{v,n=max,target}$ and the other two are combined to produce $F_{v,n=0,target}$; thus, in the case of the first two of the four flows for the $(n-1)^{th}$ component there is associated with any point in its gradient a target concentration, $[IC_{n-1,target}]$ such that $F_{v,n-1=max,n=max,target}=([IC_{n-1,target}]/[IC_{n-1=max}])*F_{v,n,target}$, is the total flow contributed by combining the flows of all the reservoirs containing $[IC_{n-1=max,n=max}]$ and $F_{v,n-1=0,n=max,target}=F_{v,n,target}-F_{v,n-1=max,n=max,target}$ is the total flow contributed by combining the flows of all the reservoirs containing $[IC_{n-1=0,n=max}]$; likewise, in the case of the other two of the four flows for the $(n-1)^{th}$ component there is associated with any point in its gradient a target concentration, $[IC_{n-1,target}]$ such that $F_{v,n-1=max,n=0,target}=([IC_{n-1,target}]/[IC_{n-1,max}])*F_{v,n=0,target}$, is the total flow contributed by combining the flows of all the reservoirs containing $[IC_{n-1=max,n=0}]$ and $F_{v,n-1=0,n=0,target}=F_{v,n=0,target}-F_{v,n-1=max,n=0,target}$ is the total flow contributed by combining the flows of all the reservoirs containing $[IC_{n-1=0,n=0}]$; thus, for the $(n-2)^{th}$ component there are eight partitioned flows: $F_{v,n-2=max,n-1=max,n=max,target}$, $F_{v,n-2=max,n-1=0,n=max,target}$, $F_{v,n-2=max,n-1=max,n=0,target}$, $F_{v,n-2=max,n-1=0,target}$, $F_{v,n-2=0,n-1=max,n=max,target}$, $F_{v,n-2=0,n-1=0,n=max,target}$, $F_{v,n-2=0,n-1=max,target}$, $F_{v,n-2=0,n-1=0,n=max,n=0,target}$; and for each of the $(n-m)^{th}$ components, $n-1 \geq m \geq 0$, there are $2^{(m+1)}$ partitioned flows defined by the same ratios derived from the target concentration value of the gradient for the $(n-m)^{th}$ component; and a) eluting the charged molecules, each of which consecutively elutes from the ion exchange stationary phase contained in the column at its effective isoelectric point; and b) collecting the charged molecules wherein each of the molecules consecutively elutes from the ion exchange stationary phase contained in the column at its effective isoelectric point until independent predetermined concentrations of each of the n IC are all reached; and c) repeating steps a)-b) as deemed necessary to separate all of the molecular species of interest.

One Hydrophilic or Mixed Mode Column, Simultaneous Generalized Multi-Component Gradients Scaled by Both Arithmetic and Manifold Function Methods In still another embodiment of the invention, there is provided a method for system for chromatographically separating charged molecules having different isoelectric points, comprising:

a computer comprising a CPU, dynamic memory, static memory and software that controls the operation of an n gradient LC separation system, $n \geq 3$; and at least $2^n$ independent fluid delivery channels $A_1, A_2, \ldots A_{2^n}$, whose fluid delivery rates are independently controlled by software running on a computer; a reservoir, $R_1$ containing an acidic buffer selected from the group consisting of the class of acidic pISep buffers, a reservoir $R_2$, containing a solution of a first IC containing an acidic buffer selected from the group consisting of the class of acidic pISep buffers; a pump $A_1$ that controls the efflux of solution from reservoir $R_1$ and a pump $A_2$ that controls the efflux of solution from reservoir $R_2$; and a reservoir, $R_3$ containing a basic buffer selected from the group consisting of the class of basic pISep buffers; and a reservoir, $R_4$, containing a basic buffer selected from the group consisting of the class of basic pISep buffers and a first IC; a pump $A_3$ that controls the efflux of solution from reservoir $R_3$ and a pump $A_4$ that controls the efflux of solution from reservoir $R_4$ and so on for a total of $R_{2^n}$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$ such that the distribution of the IC follows the following mathematical rules:

for a first component, $IC_1$ if j MOD 2=1, for all j $\ni 2^n \geq j \geq 1$, then $[IC_1]$ in $R_j=0$ else $[IC_1]$ in $R_j=$a maximum of $[IC_1]$, $[IC_{1=max}]$, attainable for the particular separation being attempted; and each of the m components $\ni n > m \geq 1$, and for all k $\ni (2^n/2^{(m-1)}) \geq k \geq 1$, then if k MOD 2=1 then if $(k*2^{(m-1)}) \geq j \geq (k*2^{(m-1)}-(2^{(m-1)}-1))$ then $R_j=0$, else $[IC_m]$ in $R_j=$a maximum of $[IC_m]$, $[IC_{m=max}]$, set by the chromatographer for the particular separation being attempted; and if m=n then for $2^{n-1} \geq j \geq 1$ the $m^{th}$ component is an basic buffer selected from the group consisting of the class of basic pISep buffers else if m=n and $2^n \geq j \geq 2^{-1}$ then the $m^{th}$ component is an acidic buffer selected from the group consisting of the class of acidic pISep buffers and a first IC; a pump $A_3$ that controls the efflux of solution from reservoir $R_3$ and a pump $A_4$ that controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$;

and at least one column containing stationary phases selected from the group of stationary phases consisting of strong anionic exchange stationary phases, strong cationic exchange stationary phases, weak anionic exchange stationary phases, weak cationic exchange stationary phases and hydrophobic stationary phases; and software configured such that if there is one column of stationary phases, then the software directs and controls:

a combined external n gradient LC method for separating charged molecules having different isoelectric points, comprising:

applying and binding the charged molecules to be separated to a column containing a cationic or anionic ion exchange stationary phase, with or without an admixture of hydrophobic binding stationary phase, perfused with an eluent comprising at least one buffering component, a first IC, a second IC, up to and including an $n-1^{th}$ IC at a predetermined initial pH and a predetermined initial concentration of the first IC and a predetermined initial concentration of the second IC up to a predetermined initial concentration of the nth IC wherein the ion exchange stationary phase has a charge opposite that of the charged molecules;

supplying to the ion exchange stationary phase contained in the column an eluent with a fixed pH starting at the initial concentration of the first IC and the initial concentration of the second IC formed from the continuous mixing of (i) a solution with the at least one buffering component pumped out from $R_1$ and a solution with a maximum predetermined concentration of the first IC containing the at least one buffering component pumped out from $R_2$, a first pair of reservoirs, and mixed so as to produce a predetermined concentration of the first IC; and (ii) a solution containing the at least one buffering component and a predetermined maximum concentration of a second IC pumped out from $R_3$ and a solution containing the at least one buffering component and both a predetermined maximum concentration of a first IC and a predetermined maximum concentration of a second IC pumped out from $R_4$, a second pair of reservoirs, and mixed so as to produce the predetermined concentration of the first IC and a predetermined maximum concentration of the second IC, wherein the mixing proportions of the solutions from the first and second pairs of reservoirs vary to maintain independent and simultaneous unretained gradients in the concentration of the first IC and the second IC each gradient with its own externally defined slope when the efflux from the two pairs are mixed and so on up to n independent simultaneous gradients such that the mixing of the n IC follows the following mathematical rules:

for the $n^{th}$ component there is associated with any pH value in its designated pH gradient a target concentration, $[IC_{n,target}]$ such that:

$F_{v,n=acidic,target} = F_u(pH, [IC_{n-1,target}], [IC_{n-2,target}] \ldots [IC_{1,target}])*F_v$, where $F_v$ is total eluent flow, $F_u$ is a multidimensional function, of the pH and all of the other $n-1$ IC, that is equal to the fraction of $F_v$ that should consist of flow containing the acidic buffer and thus $F_{v,n=acidic,target}$ is the total flow contributed by combining the flows of all the reservoirs containing $[IC_{n=acidic}]$ and $F_{v,n=basic,target} = F_v - F_{v,n=acidic,target}$ is the total flow contributed by combining the flows of all the reservoirs containing $[IC_{n=basic}]$; for the $(n-1)^{th}$ component there are four flows, two are combined to produce $F_{v,n=acidic,target}$ and the other two are combined to produce $F_{v,n=basic,target}$; thus, in the case of the first two of the four flows for the $(n-1)^{th}$ component there is associated with any point in its gradient a target concentration, $[IC_{n-1,target}]$ such that $F_{v,n-1=max,n=acidic,target} = ([IC_{n-1,target}]/[IC_{n-1=max}])*F_{v,n,target}$ is the total flow contributed by combining the flows of all the reservoirs containing $[IC_{n-1=max,n=acidic}]$ and $F_{v,n-1=0,n=acidic,target} = F_{v,n,target} - F_{v,n-1=max,n=acidic,target}$ is the total flow contributed by combining the flows of all the reservoirs containing $[IC_{n-1=0,n=acidic}]$; likewise, in the case of the other two of the four flows for the $(n-1)^{th}$ component there is associated with any point in its gradient a target concentration, $[IC_{n-1,target}]$ such that $F_{v,n-1=max,n=basic,target} = ([IC_{n-1,target}]/[IC_{n-1,max}])*F_{v,n=basic,target}$ is the total flow contribute by combining the flows of all the reservoirs containing $[IC_{n-1=max,n=basic}]$ and $F_{v,n-1=0,n=basic,target} = F_{v,n=basic,target} - F_{v,n-1=max,n=basic,target}$ is the total flow contributed by combining the flows of all the reservoirs containing $[IC_{n-1=0,n=basic}]$; thus, for the $(n-2)^{th}$ component there are eight partitioned flows: $F_{v,n-2=max,n-1=max,n=acidic,target}$, $F_{v,n-2=max,n-1=0,n=acidic,target}$, $F_{v,n-2=max,n-1=max,n=basic,target}$, $F_{v,n-2=max,n-1=0,n=basic,target}$, $F_{v,n-2=0,n-1=max,n=acidic,target}$, $F_{v,n-2=0,n-1=0,n=acidic,target}$, $F_{v,n-2=0,n-1=max,n=basic,target}$, $F_{v,n-2=0,n-1=0,n=basic,target}$; and for each of the $(n-m)^{th}$ components, $n-1 \geq m \geq 0$, there are $2^{(m+1)}$ partitioned flows defined by the same ratios derived from the target concentration value of the gradient for the $(n-m)^{th}$ component; and a) eluting the charged molecules, each of which consecutively elutes from the ion exchange stationary phase contained in the column at its effective isoelectric point; and b) collecting the charged molecules wherein each of the molecules consecutively elutes from the ion exchange stationary phase contained in the column at its effective isoelectric point until independent predetermined concentrations of each of the n IC are all reached; and c) repeating steps a)-b) as deemed necessary to separate all of the molecular species of interest.

One Hydrophilic or Mixed Mode Column and One Hydrophobic Column, Simultaneous Generalized Multi-Component Gradients Scaled by Both Arithmetic and Manifold Function Methods In still another embodiment of the invention, there is provided a method or system for chromatographically separating charged molecules having different isoelectric points, comprising:

a computer comprising a CPU, dynamic memory, static memory and software that controls the operation of an n gradient LC separation system, $n \geq 3$; and at least $2^n$ independent fluid delivery channels $A_1, A_2, \ldots A_2^n$, having fluid delivery rates that are independently controlled by software running on a computer; and a reservoir $R_1$ containing an acidic buffer selected from the group consisting of the class of acidic pISep buffers, a reservoir $R_2$ containing a solution of a first IC containing an acidic buffer selected from the group consisting of the class of acidic pISep buffers; a pump $A_1$ that controls the efflux of solution from reservoir $R_1$ and a pump $A_2$ that controls the efflux of solution from reservoir $R_2$; and a reservoir, $R_3$ containing a basic buffer selected from the group consisting of the class of basic pISep buffers; and a reservoir, $R_4$, containing a basic buffer selected from the group consisting of the class of basic pISep buffers, and a first IC; a pump $A_3$ that controls the efflux of solution from reservoir $R_3$ and a pump $A_4$ that controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$ such that the distribution of the IC follows the following mathematical rules:

for a first component, $IC_1$ if j MOD 2=1, for all j $\ni 2^n \geq j \geq 1$, then $[IC_1]$ in $R_j$=0 else $[IC_1]$ in $R_j$=a maximum of $[IC_1]$, $[IC_{1=max}]$, attainable for the particular separation being attempted; and each of the m components $\ni n > m \geq 1$, and for all k $\ni (2^n/2^{(m-1)}) \geq k \geq 1$, then if k MOD 2=1 then if $(k*2^{(m-1)}) \geq j \geq (k*2^{(m-1)}-(2^{(m-1)}-1))$ then $R_j$=0, else $[IC_m]$ in $R_j$=a maximum of $[IC_m]$, $[IC_{m=max}]$, set by the chromatographer for the particular separation being attempted; and if m=n then for $2^{n-1} \geq j \geq 1$ the $m^{th}$ component is a basic buffer selected from the group consisting of the class of basic pISep buffers, else if m=n and $2^n \geq j > 2^{n-1}$ then the $m^{th}$ component is an acidic buffer selected from the group consisting of the class of acidic pISep buffers, and a first IC; a pump $A_3$ that controls the efflux of solution from reservoir $R_3$ and a pump $A_4$ that controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$; and at least two columns containing stationary phases selected from the group of stationary phases consisting of strong anionic exchange stationary phases, strong cationic exchange stationary phases, weak anionic exchange stationary phases, weak cationic exchange stationary phases and hydrophobic stationary phases; and software configured such that if there are two columns of stationary phases, one of which is hydrophobic, then the software directs and controls:

a combined external n gradient LC method for separating charged molecules having different isoelectric points, comprising:

applying and binding the charged molecules to be separated to a first column containing a cationic or anionic ion exchange stationary phase, with or without an admixture of hydrophobic binding stationary phase, perfused with an eluent comprising at least one buffering component, a first IC, a second IC, up to and including an n-$1^{th}$ IC at a predetermined initial pH and a predetermined initial concentration of the first IC and a predetermined initial concentration of the second IC up to a predetermined initial concentration of the nth IC wherein the ion exchange stationary phase has a charge opposite that of the charged molecules;

supplying to the ion exchange stationary phase contained in the column an eluent with a fixed pH starting at the initial concentration of the first IC and the initial concentration of the second IC formed from the continuous mixing of (i) a solution with the at least one buffering component pumped out from $R_1$ and a solution with a maximum predetermined concentration of the first IC containing the at least one buffering component pumped out from $R_2$, a first pair of reservoirs, and mixed so as to produce a predetermined concentration of the first IC; and (ii) a solution containing the at least one buffering component and a predetermined maximum concentration of a second IC pumped out from $R_3$ and a solution containing the at least one buffering component and both a predetermined maximum concentration of a first IC and a predetermined maximum concentration of a second IC pumped out from $R_4$, a second pair of reservoirs, and mixed so as to produce the predetermined concentration of the first IC and a predetermined maximum concentration of the second IC, wherein the mixing proportions of the solutions from the first and second pairs of reservoirs vary to maintain independent and simultaneous unretained gradients in the concentration of the first IC and the second IC each gradient with its own externally defined slope when the efflux from the two pairs are mixed and so on up to n independent simultaneous gradients such that the mixing of the n IC follows the following mathematical rules:

for the $n^{th}$ component there is associated with any pH value in its designated pH gradient a target concentration, $[IC_{n,target}]$ such that:

$F_{v,n=acidic,target} = F_u(pH, [IC_{n-1,target}], [IC_{n-2,target}] \ldots [IC_{1,target}])*F_v$, where $F_v$ is total eluent flow, $F_u$ is a multidimensional function, of the pH and all of the other n-I IC, that is equal to the fraction of $F_v$ that should consist of flow containing the acidic buffer and thus $F_{v,n=acidic,target}$ is the total flow contributed by combining the flows of all the reservoirs containing $[IC_{n=acidic}]$ and $F_{v,n=basic,target} = F_v - F_{v,n=acidic,target}$ is the total flow contributed by combining the flows of all the reservoirs containing $[IC_{n=basic}]$; for the $(n-1)^{th}$ component there are four flows, two are combined to produce $F_{v,n=acidic,target}$ and the other two are combined to produce $F_{v,n=basic,target}$; thus, in the case of the first two of the four flows for the $(n-1)^{th}$ component there is associated with any point in its gradient a target concentration, $[IC_{n-1,target}]$ such that $F_{v,n-1=max,n=acidic,target} = ([IC_{n-1,target}]/[IC_{n-1=max}])*F_{v,n,target}$ is the total flow contributed by combining the flows of all the reservoirs containing $[IC_{n-1=max,n=acidic}]$ and $F_{v,n-1=0,n=acidic,target} = F_{v,n,target} - F_{v,n-1=max,n=acidic,target}$ is the total flow contributed by combining the flows of all the reservoirs containing $[IC_{n-1=0,n=acidic}]$; likewise, in the case of the other two of the four flows for the $(n-1)^{th}$ component there is associated with any point in its gradient a target concentration, $[IC_{n-1,target}]$ such that $F_{v,n-1=max,n=basic,target} = ([IC_{n-1,target}]/[IC_{n-1,max}])*F_{v,n=basic,target}$ is the total flow contributed by combining the flows of all the reservoirs containing $[IC_{n-1=max,n=basic}]$ and $F_{v,n-1=0,n=basic,target} = F_{v,n=basic,target} - F_{v,n-1=max,n=basic,target}$ is the total flow contributed by combining the flows of all the reservoirs containing $[IC_{n-1=0,n=basic}]$; thus, for the $(n-2)^{th}$ component there are eight partitioned flows: $F_{v,n-2=max,n-1=max,n=acidic,target}$, $F_{v,n-2=max,n-1=0,n=acidic,target}$, $F_{v,n-2=max,n-1=max,n=basic,target}$, $F_{v,n-2=max,n-1=0,n=basic,target}$, $F_{v,n-2=0,n-1=max,n=acidic,target}$, $F_{v,n-2=0,n-1=0,n=acidic,target}$, $F_{v,n-2=0,n-1=max,n=basic,target}$, $F_{v,n-2=0,n-1=0,n=basic,target}$; and for each of the $(n-m)^{th}$ components, $n-1 \geq m \geq 0$, there are $2^{(m+1)}$ partitioned flows defined by the same ratios derived from the target concentration value of the gradient for the $(n-m)^{th}$ component; and a) connecting in series after the first column containing a cationic or anionic ion exchange stationary phase a second column containing a hydrophobic stationary phase and equilibrating the stationary phases contained in the first and second columns at the initial pH and initial concentrations of the other n-1 IC;

b) supplying to the ion exchange stationary phase contained in the first column an eluent with a variable pH starting at the initial pH and an initial IC concentration formed from the continuous mixing of (i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC; repeating (b) with a second IC and up to an nth IC to create n−1 independent gradients in n−I IC plus an independent pH gradient within the first and second columns according to the mixing algorithms detailed just above;

c) eluting the charged molecules, each of which consecutively elutes from the ion exchange stationary phase contained in the first column at its effective isoelectric point until a predetermined final pH and final n−1 IC concentrations are reached;

d) directing for secondary separation the resulting effluent containing the consecutively eluted charged molecules from the first column into the hydrophobic stationary phase contained in the second column and;

e) binding the consecutively eluted charged molecules from the first column that are sufficiently hydrophobic to the hydrophobic stationary phase contained in the second column until the predetermined final pH is reached;

f) collecting the separated molecular fractions not bound to the second column g) disconnecting, as directed by software, the first column from the second column;

h) supplying to the hydrophobic stationary phase contained in the second column an eluent with a variable pH starting at the initial pH and an initial IC concentration formed from the continuous mixing of (1i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (1ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC; repeating (1i-1ii) with a second IC and up to an nth IC to create n−1 independent gradients in n−I IC plus an independent pH gradient to make a total of n independent gradients according to the mixing algorithms detailed just above;

i) collecting the charged molecules wherein each of the molecules consecutively elutes from the hydrophobic stationary phase contained in the second column according to the molecule's variation in hydrophobic binding free energy until a n−1 predetermined final concentrations of each of the n−1 IC is reached and a predetermined final pH is reached; and j) repeating steps a)-i) as deemed necessary to separate all of the molecular species of interest.

Two Hydrophilic Columns, Simultaneous Chemical Gradients, Temperature Gradients

In still another embodiment of the invention, there is provided a method or system for chromatographically separating charged molecules having different isoelectric points, comprising:

a computer comprising a CPU, dynamic memory, and static memory and software that controls the operation of a multi-pump LC separation system; and at least four independent fluid delivery channels A, B, C, and D having fluid delivery rates that are independently controlled by software running on a computer; a reservoir, $R_A$ containing an acidic buffer selected from the group consisting of the class of acidic pISep buffers; a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; and a reservoir, $R_C$ containing an acidic buffer selected from the group consisting of the class of acidic pISep buffers, and an IC; and a reservoir, $R_D$, containing a basic buffer selected from the group consisting of the class of basic pISep buffers, and an IC; a pump C that controls the efflux of acidic buffer plus IC from reservoir $R_C$ and a pump D that controls the efflux of basic buffer plus IC from reservoir $R_D$; and at least two columns containing stationary phases selected from the group of stationary phases consisting of strong anionic exchange stationary phases, strong cationic exchange stationary phases, weak anionic exchange stationary phases, and weak cationic exchange stationary phases; and software configured such that if there are two columns of stationary phases, one of which is hydrophobic, then the software directs and controls:

a combined external pH gradient LC method for separating charged molecules having different isoelectric points, comprising:

applying and binding the charged molecules to be separated to a first column containing a cationic or anionic ion exchange stationary phase perfused with an eluent comprising at least one buffering component and an IC at a predetermined initial pH measured at a temperature $T_0$ and a predetermined initial concentration of IC wherein the ion exchange stationary phase has a charge opposite that of the charged molecules;

connecting in series after the first column containing a cationic or anionic ion exchange stationary phase a second column containing a cationic or anionic ion exchange stationary phase of charge opposite to the first and equilibrating the stationary phases contained in the first and second columns at the initial pH measured at a temperature $T_0$;

supplying to the ion exchange stationary phase contained in the first column an eluent with a variable pH starting at the initial pH measured at a temperature $T_0$ according to the temperature gradient method taught in PCT/US2004/015216 (herein incorporated by reference for all purposes) and an initial IC concentration formed from the continuous mixing of (i) a solution with predetermined acidic pH measured at a temperature $T_0$ containing the at least one buffering component and an IC and a solution with predetermined acidic pH measured at a temperature $T_0$ containing the at least one buffering component and no IC pumped out from a first pair of reservoirs and mixed so as to produce a predetermined concentration of IC and (ii) a solution at a predetermined basic pH measured at a temperature $T_0$ containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC and both gradients subjected to a temperature gradient from a temperature $T_1$ to a temperature $T_2$ wherein the temperature $T_1$ is the temperature of the stationary phase where the eluent enters the stationary phase and the temperature $T_2$ is the temperature where the eluent exits the stationary phase according to the temperature gradient method taught in PCT/US2004/015216;

a) eluting the charged molecules, subjected to a temperature gradient from a temperature $T_1$ to a temperature $T_2$ wherein the temperature $T_1$ is the temperature of the stationary phase where the eluent enters the stationary phase and the temperature $T_2$ is the temperature where the eluent exits the stationary phase, each of which consecutively elutes from the ion exchange stationary phase contained in the first column at its effective isoelectric point until a predetermined final pH and a predetermined concentration of IC is reached;

b) directing for secondary separation the resulting effluent containing the consecutively eluted charged molecules from the first column into the ion exchange stationary phase contained in the second column subjected to a temperature gradient from a temperature $T_3$ to a temperature $T_4$ wherein the temperature $T_3$ is the temperature of the exchange stationary phase in the second column where the effluent from the exchange stationary phase of the first column enters the absorbent in the second column and the temperature $T_4$ is the temperature where the effluent exits the exchanger in the second column and equilibrating both exchangers at the initial maximum pH as measured at the temperature T0 according to the temperature gradient method taught in PCT/US2004/015216 and;

c) binding the charged molecules that are oppositely charged to the ion exchange stationary phase contained in the second column until the predetermined final pH and the predetermined concentration of IC is reached is reached;

d) disconnecting, as directed by software, the first column from the second column;

e) reversing the pH gradient perfusing the ion exchange stationary phase contained in the second column to develop a second predetermined final pH from a second predetermined initial pH and simultaneously developing a second predetermined final IC concentration from a second predetermined initial IC concentration; and f) collecting the charged molecules wherein each of the molecules consecutively elutes from the ion exchange stationary phase contained in the second column, subjected to a temperature gradient from a temperature $T_3$ to a temperature $T_4$ wherein the temperature $T_3$ is the temperature of the exchange stationary phase in the second column where the effluent from the exchange stationary phase of the first column enters the absorbent in the second column and the temperature $T_4$ is the temperature where the effluent exits the exchanger in the second column and equilibrating both exchangers at the initial maximum pH as measured at the temperature $T_0$, at its effective isoelectric point until the second predetermined final pH and the second predetermined final IC concentration is reached: and g) optionally reconnecting by direction of software in series after the first column a second column containing an ion exchange stationary phase of the opposite charge to the stationary phase contained in the first column and equilibrating the ion exchange stationary phases contained in the first and second columns at the initial pH; and h) repeating steps a)-g) as deemed necessary to separate all of the molecular species of interest.

One Anionic Electrochromatofocussing Column

The excess temperature, $\Delta T$, developed in a packed ion exchange column subject to a voltage gradient is given by:

$$\Delta T = Q d^2_{col} / 16K \quad \text{(Eqn. 1)}$$

where Q is the heat per cm generated by the passage of the electric current through the column, $d_{col}$ is the inside diameter of the column and K is the thermal conductivity of the solution in the column. The thermal conductivity of the buffer systems is approximately that of pure water or ~0.006 W*cm$^{-1}$ deg$^{-1}$ so 16K is ~0.1 W*cm$^{-1}$ deg$^{-1}$. In an embodiment of the invention utilizing a preferred set of pISep buffers with added NaOH in the alkaline buffers, the resistance of the packed strong anionic and cationic columns will be essentially constant at 50 $\Omega$*cm$^{-1}$. A voltage gradient of 25 volts*cm$^{-1}$ along the length of a 2 cm column would then produce a current of 0.5 ampere. The power dissipation would be 12.5 watts*cm$^{-1}$ and with $d^2_{col}$=0.25 cm$^{-2}$, $\Delta T \approx 30$ deg. Thus an ice bath will allow operation of the system at these voltages and ~ ambient temperature internally in the packed column.

The ionic mobility of $H^+$ is ~4.25*10$^{-10}$ coulomb*sec*gm$^{-1}$ and one volt*cm$^{-1}$=10$^7$*gm*cm*sec$^{-2}$coulomb$^{-1}$. Thus a gradient of volt*cm$^{-1}$ will produce an $H^+$ flow of about 40 μm*sec$^{-1}$ and 25 volt*cm$^{-1}$ will produce a flow of ~1 mm*sec$^{-1}$. This comparable to the typical flow in analytic FPLC and HPLC columns. In the case of anionic exchange this initial flow will be opposed by the sum of the bulk and electroosmotic flow. The general differential equation describing the $H^+$ flux in this system is just a modified form of Fick's first law and at steady state the equation is everywhere equal to a constant flux, $J_x$. It is:

$$-D * \frac{\partial [H^+]}{\partial x} + (V_B + V_{ee} + u_H E) * [H^+] = J_x$$

Where D is the diffusion constant for, $V_B$ is the pressure induced flow, $V_{ee}$ is the electroosmotic flow, $u_H$ is the hydrogen ion mobility and E is the voltage gradient. The general solution is:

$$[H^+(x)] = \frac{J_x + ((V_B + V_{ee} + u_H E) * [H^+(0)] - J_x) * e^{\frac{(V_B + V_{ee} + u_H E) * x}{D}}}{(V_B + V_{ee} + u_H E)}$$

In the simplest case on an anionic column $(V_B + V_{ee} + u_H E) = (V_B + V_{ee} - u_H |E|)$ and this will approach zero at voltage gradients close to 25 volts*cm$^{-1}$ when the pumping rate is also ~1 mm*sec$^{-1}$. In this case the steady state $H^+$ gradient is linear:

$$[H^+(x)] = [H^+(0)] - \frac{J_x * x}{D}$$

This means that in this special case the flow of hydrogen ions down the column is strictly Fickian diffusion. Mass balance then dictates that $J_x = V_B * [H^+]_B$ i.e. the flow down the column equals the flow of $H^+$ being pumped in from the reservoirs. Thus the steady state concentration at the efflux end of the column of length l will be $[H^+]_B$ and $$[H^+(0)] = [H^+]_B + \frac{J_x * l}{D}.$$

Over the length of a typical 50 mm FPLC column this would produce a pH drop of more than 3 pH units independent of the slope of the pH gradient being pumped out from the reservoirs. Thus, for an incoming gradient changing at 0.01 pH units $CV^{-1}$ the peak sharpening would be expected to exceed an order of magnitude. However, since the peak sharpening is proportional to the square root of the slope of the pH gradient in the column, this implies that very significant gains in resolution could be achieved by much lower voltage gradients, obviating the need for column cooling of typical analytic FPLC or HPLC columns; and yielding another embodiment of the invention, which provides a method or system for chromatographically separating charged molecules having different isoelectric points, comprising:

a computer comprising a CPU, dynamic memory, static memory and software that controls the operation of a multi-pump chromatographic separation system; and at least two independent fluid delivery channels A and B, having fluid delivery rates that are independently controlled by software running on a computer; a reservoir, $R_A$ containing an acidic buffer selected from the group consisting of the class of acidic pISep buffers; a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; and at least one column containing stationary phases selected from the group of stationary phases consisting of strong anion exchange stationary phases and weak anionic exchange stationary phases; and the at least one column containing stationary phases has an electrode at the opening or connected to the opening by a sealed bridge where the mixture of buffers from A and B enters the column; and a second electrode at the opening or connected by a sealed bridge to the efflux end of the column such that software on a computer directs and controls:

a method of chromatographically separating charged molecules having different isoelectric points, comprising:

applying and binding the charged molecules to be separated to an anion exchange stationary phase perfused with a solvent comprising at least one buffering component at a predetermined initial pH where the ion exchange stationary phase has a charge opposite that of the charged molecules and one isocratic component, hereafter designated as an IC, at concentration from zero to a predetermined maximum concentration, selected from the group of components consisting of nonionic detergents, ionic detergents, polar organic molecules, nonpolar organic molecules, acids, bases, neutral salts, acidic salts and basic salts;

generating an electrical potential in the along the longitudinal axis of the column so as to create a gradient of pH within the column of increasing alkalinity towards the efflux end of the column relative to the influx end and in addition to the gradient ordinarily present due the finite time necessary for incoming effluent to traverse the length of the column;

supplying to the ion exchange stationary phase an eluent with a variable pH starting at the initial pH formed from the continuous mixing of (i) a solution at a predetermined acidic pH containing the at least one buffering component and an IC pumped out from a first reservoir with (ii) a solution at a predetermined alkaline pH containing the at least one buffering component and an IC pumped out from a second reservoir, wherein the mixing proportions of the solutions from the first and second reservoirs vary to maintain an unretained pH gradient with an externally defined slope at the influx end of the column; and directing the application of a positive electrical potential at the efflux end of the column acting to produce a current flow in the column and a consequent ascending pH gradient through the length of the column and an associated electroosmotic flow concurrent with the flow induced externally by the pumps driving the fluid delivery system through channels A and B; and collecting the charged molecules until a predetermined final pH is reached, wherein each of the molecules consecutively elutes from the ion exchange stationary phase at its effective isoelectric point.

One Cationic Electrochromatofocussing Column

In the case of cationic exchange the electrical $H^+$ flow will sum with the bulk and electroosmotic flow. In this case the general solution for the steady state pH gradient:

$$[H^+(x)] = \frac{J_x + ((V_B + V_{ee} + u_H E) * [H^+(0)] - J_x) * e^{\frac{(V_B + V_{ee} + u_H E) * x}{D}}}{(V_B + V_{ee} + u_H E)}$$

is of no practical interest since the exponential term is of enormous, unphysical magnitude. Nevertheless, it can be expected that a significant positive slope pH gradient will form as a result of electric field gradients of the same magnitude as used in the anionic columns;

yielding another embodiment of the invention, which provides a method or system for chromatographically separating charged molecules having different isoelectric points, comprising:

a computer comprising a CPU, dynamic memory, static memory and software that controls the operation of a multi-pump chromatographic separation system; and at least two independent fluid delivery channels A and B, having fluid delivery rates that are independently controlled by software running on a computer; and a reservoir, $R_A$ containing an acidic buffer selected from the group consisting of the class of acidic pISep buffers; a reservoir, $R_B$, containing a basic buffer selected from the group consisting of the class of basic pISep buffers; a pump A that controls the efflux of acidic buffer from reservoir $R_A$ and a pump B that controls the efflux of basic buffer from reservoir $R_B$; and at least one column containing stationary phases selected from the group of stationary phases consisting of strong cationic exchange stationary phases and weak cationic exchange stationary phases; and the at least one column containing stationary phases has an electrode at the opening or connected to the opening by a sealed bridge where the mixture of buffers from A and B enters the column and a second electrode at the opening or connected by a sealed bridge to the efflux end of the column such that software on a computer directs and controls:

a method of chromatographically separating charged molecules having different isoelectric points, comprising:

applying and binding the charged molecules to be separated to an cation exchange stationary phase perfused with a solvent comprising at least one buffering component at a predetermined initial pH where the ion exchange stationary phase has a charge opposite that of the charged molecules and one isocratic component, hereafter designated as an IC, at concentration from zero to a predetermined maximum concentration, selected from the group of components consisting of nonionic detergents, ionic detergents, polar organic molecules, nonpolar organic molecules, acids, bases, neutral salts, acidic salts and basic salts;

generating an electrical potential in the along the longitudinal axis of the column so as to create a gradient of pH within the column of increasing acidity towards the efflux end of the column relative to the influx end and in addition to the gradient ordinarily present due the finite time necessary for incoming effluent to traverse the length of the column;

supplying to the ion exchange stationary phase an eluent with a variable pH starting at the initial pH formed from the continuous mixing of (i) a solution at a predetermined acidic pH containing the at least one buffering component and an IC pumped out from a first reservoir with (ii) a solution at a predetermined alkaline pH containing the at least one buffering component and an IC pumped out from a second reservoir, wherein the mixing proportions of the solutions from the first and second reservoirs vary to maintain an unretained pH gradient with an externally defined slope at the influx end of the column;

directing the application of a positive electrical potential at the efflux end of the column acting to produce a current flow in the column and a consequent ascending pH gradient through the length of the column and an associated electroosmotic flow concurrent with the flow induced externally by the pumps driving the fluid delivery system through channels A and B; and collecting the charged molecules until a predetermined final pH is reached, wherein each of the molecules consecutively elutes from the ion exchange stationary phase at its effective isoelectric point.

One Anionic Electrochromatofocussing Column Simultaneous Generalized Multi-Component Gradients Scaled Arithmetically Yet another embodiment of the invention provides a method or system for chromatographically separating charged molecules having different isoelectric points, comprising:

a computer comprising a CPU, dynamic memory, static memory and software that controls the operation of an n gradient chromatographic separation system, $n \geq 3$; and at least $2^n$ independent fluid delivery channels $A_1, A_2, \ldots A_2^n$, having fluid delivery rates that are independently controlled by software running on a computer; a reservoir, $R_1$ containing a solution at a buffered pH and a reservoir, $R_2$, containing a solution of a first IC at a buffered pH; a pump $A_1$ that controls the efflux of solution from reservoir $R_1$ and a pump $A_2$ that controls the efflux of solution from reservoir $R_2$; and a reservoir, $R_3$ containing a solution of a second IC at a buffered pH; and a reservoir, $R_4$, containing a solution of a first IC and a second IC at a buffered pH; a pump $A_3$ that controls the efflux of efflux of solution from reservoir $R_3$ and a pump $A_4$ that controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary $m^{th}$ subset of $2^{n-1}$ reservoirs not containing that $IC_m$ such that the distribution of the IC follows the following mathematical rules:

for a first component, $IC_1$, if j MOD 2=1, for all j $\ni 2^n \geq j \geq 1$, then $[IC_1]$ in $R_j$=0 else $[IC_1]$ in $R_j$=a maximum of $[IC_1]$, $[IC_{1=max}]$, attainable for the particular separation being attempted; and each of the m components $\ni n \geq m > 1$, and for all k $\ni (2^n/2^{(m-1)}) \geq k \geq 1$, then if k MOD 2=1 then if $(k*2^{(m-1)}) \geq j \geq (k*2^{(m-1)}-(2^{(m-1)}-1))$ then $R_j$=0, else $[IC_m]$ in $R_j$=a maximum of $[IC_m]$, $[IC_{m=max}]$, set by the chromatographer for the particular separation being attempted and at least one column containing stationary phases selected from the group of stationary phases consisting of strong anionic exchange stationary phases and weak anionic exchange stationary phases; and software configured such that if there is one column of stationary phases, and the at least one column containing stationary phases has an electrode at the opening or connected to the opening by a sealed bridge where the mixture of buffers from the at least $2^n$ independent fluid delivery channels $A_1, A_2, \ldots A_2^n$ enters the column and a second electrode at the opening or connected by a sealed bridge to the efflux end of the column then software directs and controls:

a combined external n gradient chromatographic method for separating charged molecules having different isoelectric points, comprising:

applying and binding the charged molecules to be separated to a column containing an anionic ion exchange stationary phase perfused with an eluent comprising at least one buffering component, a first IC, a second IC, up to and including an nth IC at a predetermined initial pH and a predetermined initial concentration of the first IC and a predetermined initial concentration of the second IC up to a predetermined initial concentration of the nth IC wherein the ion exchange stationary phase has a charge opposite that of the charged molecules;

generating an electrical potential in the along the longitudinal axis of the column so as to create a gradient of pH within the column of increasing alkalinity towards the efflux end of the column relative to the influx end and in addition to the gradient ordinarily present due the finite time necessary for incoming effluent to traverse the length of the column;

supplying to the ion exchange stationary phase contained in the column an eluent with a fixed pH starting at the initial concentration of the first IC and the initial concentration of the second IC formed from the continuous mixing of (i) a solution with the at least one buffering component pumped out from $R_1$ and a solution with a maximum predetermined concentration of the first IC containing the at least one buffering component pumped out from $R_2$, a first pair of reservoirs, and mixed so as to produce a predetermined concentration of the first IC; and (ii) a solution containing the at least one buffering component and a predetermined maximum concentration of a second IC pumped out from $R_3$ and a solution containing the at least one buffering component and both a predetermined maximum concentration of a first IC and a predetermined maximum concentration of a second IC pumped out from $R_4$, a second pair of reservoirs, and mixed so as to produce the predetermined concentration of the first IC and a predetermined maximum concentration of the second IC, wherein the mixing proportions of the solutions from the first and second pairs of reservoirs vary to maintain independent and simultaneous unretained gradients in the concentration of the first IC and the second IC each gradient with its own externally defined slope when the efflux from the two pairs are mixed and so on up to n independent simultaneous gradients such that the mixing of the n IC follows the following mathematical rules:

for the $n^{th}$ component there is associated with any point in its gradient a target concentration, $[IC_{n,target}]$ such that $F_{v,n=max,target} = ([IC_{n,target}]/[IC_{n=max}])*F_v$, where $F_v$ is total eluent flow, and $F_{v,n=max,target}$ is the total flow contributed by combining the flows of all the reservoirs containing $[IC_{n=max}]$ and $F_{v,n=0,target} = F_v - F_{v,n=max,target}$ is the total flow contributed by combining the flows of all the reservoirs containing $[IC_{n=0}]$; for the $(n-1)^{th}$ component there are four flows, two are combined to produce $F_{v,n=max,target}$ and the other two are combined to produce $F_{v,n=0,target}$; thus, in the case of the first two of the four flows for the $(n-1)^{th}$ component there is associated with any point in its gradient a target concentration, $[IC_{n-1,target}]$ such that $F_{v,n-1=max,n=max,target} = ([IC_{n-1,target}]/[IC_{n-1=max}])*F_{v,n,target}$, is the total flow contributed by combining the flows of all the reservoirs containing $[IC_{n-1=max,n=max}]$ and $F_{v,n-1=0,n=max,target}=F_{v,n,target}-F_{v,n-1=max,n=max,target}$ is the total flow contributed by combining the flows of all the reservoirs containing $[IC_{n-1=0,n=max}]$; likewise, in the case of the other two of the four flows for the $(n-1)^{th}$ component there is associated with any point in its gradient a target concentration, $[IC_{n-1,target}]$ such that $F_{v,n-1=max,n=0,target}=([IC_{n-1,target}]/[IC_{n-1,max}])^* F_{v,n=0,target}$, is the total flow contributed by combining the flows of all the reservoirs containing $[IC_{n-1=max,n=0}]$ and $F_{v,n-1=0,n=0,target}=F_{v,n=0,target}-F_{v,n-1=max,n=0,target}$ is the total flow contributed by combining the flows of all the reservoirs containing $[IC_{n-1=0,n=0}]$; thus, for the $(n-2)^{th}$ component there are eight partitioned flows: $F_{v,n-2=max,n-1=max,n=max,target}$, $F_{v,n-2=max,n-1=0,n=max,target}$, $F_{v,n-2=max,n-1=max,n=0,target}$, $F_{v,n-2=max,n-1=0,n=0,target}$, $F_{v,n-2=0,n-1=max,n=max,target}$, $F_{v,n-2=0,n-1=0,n=max,target}$, $F_{v,n-2=0,n-1=max,n=0,target}$, $F_{v,n-2=0,n-1=0,n=0,target}$; and for each of the $(n-m)^{th}$ components, $n-1 \geq m \geq 0$, there are $2^{(m+1)}$ partitioned flows defined by the same ratios derived from the target concentration value of the gradient for the $(n-m)^{th}$ component; and a) eluting the charged molecules, each of which consecutively elutes from the ion exchange stationary phase contained in the column at its effective isoelectric point; and b) collecting the charged molecules wherein each of the molecules consecutively elutes from the ion exchange stationary phase contained in the column at its effective isoelectric point until independent predetermined concentrations of each of the n IC are all reached; and c) repeating steps a)-b) as deemed necessary to separate all of the molecular species of interest.

One Cationic Electrochromatofocussing Column Simultaneous Generalized Multi-Component Gradients Scaled Arithmetically Yet another embodiment of the invention provides a method or system for chromatographically separating charged molecules having different isoelectric points, comprising:

a computer having a CPU, dynamic memory, static memory and software that controls the operation of an n gradient chromatographic separation system, $n \geq 3$; and at least $2^n$ independent fluid delivery channels $A_1, A_2, \ldots A_2^n$, having fluid delivery rates that are independently controlled by software running on a computer; a reservoir, $R_1$ containing a solution at a buffered pH and a reservoir, $R_2$, containing a solution of a first IC at a buffered pH; a pump $A_1$ that controls the efflux of solution from reservoir $R_1$ and a pump $A_2$ that controls the efflux of solution from reservoir $R_2$; and a reservoir, $R_3$ containing a solution of a second IC at a buffered pH; and a reservoir, $R_4$, containing a solution of a first IC and a second IC at a buffered pH; a pump $A_3$ that controls the efflux of solution from reservoir $R_3$ and a pump $A_4$ that controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary $m^{th}$ subset of $2^{n-1}$ reservoirs not containing that $IC_m$ such that the distribution of the IC follows the following mathematical rules:

for a first component, $IC_1$, if j MOD 2=1, for all j $\ni 2^n \geq j \geq 1$, then $[IC_1]$ in $R_j=0$ else $[IC_1]$ in $R_j=$a maximum of $[IC_1]$, $[IC_{1=max}]$, attainable for the particular separation being attempted; and each of the m components $\ni n \geq m > 1$, and for all k $\ni (2^n/2^{(m-1)}) \geq k \geq 1$, then if k MOD 2=1 then if $(k*2^{(m-1)}) \geq j \geq (k*2^{(m-1)}-(2^{(m-1)}-1))$ then $R_j=0$, else $[IC_m]$ in $R_j=$a maximum of $[IC_m]$, $[IC_{m=max}]$, set by the chromatographer for the particular separation being attempted;

and at least one column containing a stationary phase selected from the group of stationary phases consisting of strong cationic exchange stationary phases and weak cationic exchange stationary phases; and software configured such that if there is one column of a stationary phase, and the at least one column containing a stationary phase has an electrode at the opening or connected to the opening by a sealed bridge where the mixture of buffers from the at least $2^n$ independent fluid delivery channels $A_1, A_2, \ldots A_2^n$ enters the column and a second electrode at the opening or connected by a sealed bridge to the efflux end of the column then software directs and controls:

a combined external n gradient chromatographic method for separating charged molecules having different isoelectric points, comprising:

applying and binding the charged molecules to be separated to a column containing an cationic ion exchange stationary phase perfused with an eluent comprising at least one buffering component, a first IC, a second IC, up to and including an nth IC at a predetermined initial pH and a predetermined initial concentration of the first IC and a predetermined initial concentration of the second IC up to a predetermined initial concentration of the nth IC wherein the ion exchange stationary phase has a charge opposite that of the charged molecules;

generating an electrical potential along the longitudinal axis of the column so as to create a gradient of pH within the column of increasing acidity towards the efflux end of the column relative to the influx end and in addition to the gradient ordinarily present due to the finite time necessary for incoming effluent to traverse the length of the column;

supplying to the ion exchange stationary phase contained in the column an eluent with a fixed pH starting at the initial concentration of the first IC and the initial concentration of the second IC formed from the continuous mixing of (i) a solution with the at least one buffering component pumped out from $R_1$ and a solution with a maximum predetermined concentration of the first IC containing the at least one buffering component pumped out from $R_2$, a first pair of reservoirs, and mixed so as to produce a predetermined concentration of the first IC; and (ii) a solution containing the at least one buffering component and a predetermined maximum concentration of a second IC pumped out from $R_3$ and a solution containing the at least one buffering component and both a predetermined maximum concentration of a first IC and a predetermined maximum concentration of a second IC pumped out from $R_4$, a second pair of reservoirs, and mixed so as to produce the predetermined concentration of the first IC and a predetermined maximum concentration of the second IC, wherein the mixing proportions of the solutions from the first and second pairs of reservoirs vary to maintain independent and simultaneous unretained gradients in the concentration of the first IC and the second IC each gradient with its own externally defined slope when the efflux from the two pairs are mixed and so on up to n independent simultaneous gradients such that the mixing of the n IC follows the following mathematical rules:

for the $n^{th}$ component there is associated with any point in its gradient a target concentration, $[IC_{n,target}]$ such that:

$F_{v,n=max,target}=([IC_{n,target}]/[IC_{n=max}])^*F_v$, where $F_v$ is total eluent flow, and $F_{v,n=max,target}$ is the total flow contributed by combining the flows of all the reservoirs containing $[IC_{n=max}]$ and $F_{v,n=0,target}=F_v-F_{v,n=max,target}$ is the total flow contributed by combining the flows of all the reservoirs containing

[$IC_{n=0}$]; for the $(n-1)^{th}$ component there are four flows, two are combined to produce $F_{v,n=max,target}$ and the other two are combined to produce $F_{v,n=0,target}$; thus, in the case of the first two of the four flows for the $(n-1)^{th}$ component there is associated with any point in its gradient a target concentration, [$IC_{n-1,target}$] such that $F_{v,n-1=max,n=max,target}=$ ([$IC_{n-1,target}$]/[$IC_{n-1=max}$])*$F_{v,n,target}$, is the total flow contributed by combining the flows of all the reservoirs containing [$IC_{n-1=max,n=max}$] and $F_{v,n-1=0,n=max,target}=F_{v,n,target}-F_{v,n-1=max,n=max,target}$ is the total flow contributed by combining the flows of all the reservoirs containing [$IC_{n-1=0,n=max}$]; likewise, in the case of the other two of the four flows for the $(n-1)^{th}$ component there is associated with any point in its gradient a target concentration, [$IC_{n-1,target}$] such that $F_{v,n-1=max,n=0,target}=$([$IC_{n-1,target}$]/[$IC_{n-1,max}$])*$F_{v,n=0,target}$, is the total flow contributed by combining the flows of all the reservoirs containing [$IC_{n-1=max,n=0}$] and $F_{v,n-1=0,n=0,target}=F_{v,n=0,target}-F_{v,n-1=max,n=0,target}$ is the total flow contributed by combining the flows of all the reservoirs containing [$IC_{n-1=0,n=0}$]; thus, for the $(n-2)^{th}$ component there are eight partitioned flows: $F_{v,n-2=max,n-1=max,n=max,target}$, $F_{v,n-2=max,n-1=0,n=max,target}$, $F_{v,n-2=max,n-1=max,n=0,target}$, $F_{v,n-2=max,n-1=0,n=0,target}$, $F_{v,n-2=0,n-1=max,n=max,target}$, $F_{v,n-2=0,n-1=0,n=max,target}$, $F_{v,n-2=0,n-1=max,n=0,target}$, $F_{v,n-2=0,n-1=0,n=0,target}$; and for each of the $(n-m)^{th}$ components, $n-1 \geq m \geq 0$, there are $2^{(m+1)}$ partitioned flows defined by the same ratios derived from the target concentration value of the gradient for the $(n-m)^{th}$ component; and a) eluting the charged molecules, each of which consecutively elutes from the ion exchange stationary phase contained in the column at its effective isoelectric point; and b) collecting the charged molecules wherein each of the molecules consecutively elutes from the ion exchange stationary phase contained in the column at its effective isoelectric point until independent predetermined concentrations of each of the n IC are all reached; and c) repeating steps a)-b) as necessary to separate all of the molecular species of interest.

One Ion Exchange Electrochromatofocussing Column Simultaneous Generalized Multi-Component Gradients Scaled by Both Arithmetic and Manifold Function Methods In still another embodiment of the invention, there is provided a method or system for chromatographically separating charged molecules having different isoelectric points, comprising:

a computer comprising a CPU, dynamic memory, static memory and software that controls the operation of an n gradient chromatographic separation system $n \geq 3$, with a variable electric gradient; and at least $2^n$ independent fluid delivery channels $A_1, A_2, \ldots A_2^n$, having fluid delivery rates that are independently controlled by software running on a computer; a reservoir, $R_1$ containing an acidic buffer selected from the group consisting of the class of acidic pISep buffers; a reservoir $R_2$, containing a solution of a first IC containing an acidic buffer selected from the group consisting of the class of acidic pISep buffers; a pump $A_1$ that controls the efflux of solution from reservoir $R_1$ and a pump $A_2$ that controls the efflux of solution from reservoir $R_2$; and a reservoir, $R_3$ containing a basic buffer selected from the group consisting of the class of basic pISep buffers; and a reservoir, $R_4$, containing a basic buffer selected from the consisting of the class of basic pISep buffers, and a first IC; a pump $A_3$ that controls the efflux of solution from reservoir $R_3$ and a pump $A_4$ that controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$ such that the distribution of the IC follows the following mathematical rules:

for a first component, $IC_1$ if j MOD 2=1, for all j $\ni 2^n \geq j \geq 1$, then [$IC_1$] in $R_j=0$ else [$IC_1$] in $R_j=$a maximum of [$IC_1$], [$IC_{1=max}$], attainable for the particular separation being attempted; and each of the m components $\ni n > m \geq 1$, and for all k $\ni (2^n/2^{(m-1)}) \geq k \geq 1$, then if k MOD 2=1 then if $(k*2^{(m-1)}) \geq j \geq (k*2^{(m-1)}-(2^{(m-1)}-1))$ then $R_j=0$, else [$IC_m$] in $R_j=$a maximum of [$IC_m$], [$IC_{m=max}$], set by the chromatographer for the particular separation being attempted; and if m=n then for $2^{n-1} \geq j \geq 1$ the $m^{th}$ component is an basic buffer from the class of basic pISep buffers else if m=n and $2^n \geq j > 2^{n-1}$ then the $m^{th}$ component is an acidic buffer from the class of acidic pISep buffers and a first IC such that a pump $A_3$ controls the efflux of solution from reservoir $R_3$ and a pump $A_4$ controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$;

and a column containing a stationary phase selected from the group of stationary phases consisting of strong anionic exchange stationary phases, weak anionic exchange stationary phases, strong cationic exchange stationary phases, weak cationic exchange stationary phases; and software configured such that if there is one column of ion exchange stationary phase, and the at least one column containing an ion exchange stationary phase has an electrode at the opening or connected to the opening by a sealed bridge where the mixture of buffers from the at least $2^n$ independent fluid delivery channels $A_1, A_2, \ldots A_2^n$ enters the column and a second electrode at the opening or connected by a sealed bridge to the efflux end of the column then software directs and controls:

a combined external n gradient chromatographic method for separating charged molecules having different isoelectric points, comprising:

applying and binding the charged molecules to be separated to the column containing an ion exchange stationary phase perfused with an eluent comprising at least one buffering component, a first IC, a second IC, up to and including an $n-1^{th}$ IC at a predetermined initial pH and a predetermined initial concentration of the first IC and a predetermined initial concentration of the second IC up to a predetermined initial concentration of the nth IC wherein the ion exchange stationary phase has a charge opposite that of the charged molecules;

generating an electrical potential in the along the longitudinal axis of the column so as to create a gradient of pH within the column of increasing alkalinity towards the efflux end of the column relative to the influx end, if the ion exchange stationary phase is an anion exchanger, or generating an electrical potential in the along the longitudinal axis of the column so as to create a gradient of pH within the column of decreasing alkalinity towards the efflux end of the column relative to the influx end, if the ion exchange stationary phase is a cation exchanger, and in addition to the gradient ordinarily present due the finite time necessary for incoming effluent to traverse the length of the column;

One Hydrophilic or Mixed Mode Anionic
Electrochromatofocussing Column and One
Hydrophobic Column, Simultaneous Generalized
Multi-Component Gradients Scaled by Both
Arithmetic and Manifold Function Methods In still another embodiment of the invention, there is provided a method or system for chromatographically separating charged molecules having different isoelectric points, comprising:

a computer comprising a CPU, dynamic memory, static memory and software that controls the operation of an n gradient chromatographic separation system $n \geq 3$, with a variable electric gradient; and at least $2_n$ independent fluid delivery channels $A_1, A_2, \ldots A_2^n$, having fluid delivery rates that are independently controlled by software running on a computer; a reservoir, $R_1$ containing an acidic buffer selected from the group consisting of the class of acidic pISep buffers; a reservoir $R_2$, containing a solution of a first IC containing an acidic buffer selected from the group consisting of the class of acidic pISep buffers; a pump $A_1$ that controls the efflux of solution from reservoir $R_1$ and a pump $A_2$ that controls the efflux of solution from reservoir $R_2$; and a reservoir, $R_3$ containing a basic buffer selected from the group consisting of the class of basic pISep buffers; and a reservoir, $R_4$, containing a basic buffer selected from the consisting of the class of basic pISep buffers, and a first IC; a pump $A_3$ that controls the efflux of solution from reservoir $R_3$ and a pump $A_4$ that controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$ such that the distribution of the IC follows the following mathematical rules:

for a first component, $IC_1$ if j MOD 2=1, for all j $\ni 2^n \geq j \geq 1$, then $[IC_1]$ in $R_j$=0 else $[IC_1]$ in $R_j$=a maximum of $[IC_1]$, $[IC_{1=max}]$, attainable for the particular separation being attempted; and each of the m components $\ni n>m \geq 1$, and for all k $\ni (2^n/2^{(m-1)}) \geq k \geq 1$, then if k MOD 2=1 then if $(k*2^{(m-1)}) \geq j \geq (k*2^{(m-1)}-(2^{(m-1)}-1))$ then $R_j$=0, else $[IC_m]$ in $R_j$=a maximum of $[IC_m]$, $[IC_{m=max}]$, set by the chromatographer for the particular separation being attempted; and if m=n then for $2^{n-1} \geq j \geq 1$ the $m^{th}$ component is an basic buffer from the class of basic pISep buffers else if m=n and $2^n \geq j > 2^{n-1}$ then the $m^{th}$ component is an acidic buffer from the class of acidic pISep buffers and a first IC such that a pump $A_3$ controls the efflux of solution from reservoir $R_3$ and a pump $A_4$ controls the efflux of solution from reservoir $R_4$ and so on for a total of $R_2^n$ reservoirs such that for the gradient of the $m^{th}$ IC of the n, $IC_m$, $n \geq m \geq 1$, there is a unique $m^{th}$ subset of $2^{n-1}$ independent reservoirs containing, and complementary subset of $2^{n-1}$ reservoirs not containing that $IC_m$;

and at least two columns containing stationary phases selected from the group of stationary phases consisting of strong anionic exchange stationary phases, weak anionic exchange stationary phases and hydrophobic stationary phases; and software configured such that if there is one column of anionic stationary phases, and the at least one column containing anion exchange stationary phases has an electrode at the opening or connected to the opening by a sealed bridge where the mixture of buffers from the at least $2^n$ independent fluid delivery channels $A_1, A_2, \ldots A_2^n$ enters the column and a second electrode at the opening or connected by a sealed bridge to the efflux end of the column then software directs and controls:

a combined external n gradient chromatographic method for separating charged molecules having different isoelectric points, comprising:

applying and binding the charged molecules to be separated to a first column containing an anionic ion exchange stationary phase, with or without an admixture of hydrophobic stationary phase, perfused with an eluent comprising at least one buffering component, a first IC, a second IC, up to and including an $n-1^{th}$ IC at a predetermined initial pH and a predetermined initial concentration of the first IC and a predetermined initial concentration of the second IC up to a predetermined initial concentration of the nth IC wherein the ion exchange stationary phase has a charge opposite that of the charged molecules;

generating an electrical potential in the along the longitudinal axis of the column so as to create a gradient of pH within the column of increasing alkalinity towards the efflux end of the column relative to the influx end and in addition to the gradient ordinarily present due the finite time necessary for incoming effluent to traverse the length of the column;

supplying to the ion exchange stationary phase contained in the column an eluent with a fixed pH starting at the initial concentration of the first IC and the initial concentration of the second IC formed from the continuous mixing of (i) a solution with the at least one buffering component pumped out from $R_1$ and a solution with a maximum predetermined concentration of the first IC containing the at least one buffering component pumped out from $R_2$, a first pair of reservoirs, and mixed so as to produce a predetermined concentration of the first IC; and (ii) a solution containing the at least one buffering component and a predetermined maximum concentration of a second IC pumped out from $R_3$ and a solution containing the at least one buffering component and both a predetermined maximum concentration of a first IC and a predetermined maximum concentration of a second IC pumped out from $R_4$, a second pair of reservoirs, and mixed so as to produce the predetermined concentration of the first IC and a predetermined maximum concentration of the second IC, wherein the mixing proportions of the solutions from the first and second pairs of reservoirs vary to maintain independent and simultaneous unretained gradients in the concentration of the first IC and the second IC each gradient with its own externally defined slope when the efflux from the two pairs are mixed and so on up to n independent simultaneous gradients such that the mixing of the n IC follows the following mathematical rules:

for the $n^{th}$ component there is associated with any pH value in its designated pH gradient a target concentration, $[IC_{n,target}]$ such that:

$F_{v,n=acidic,target}=F_u(pH, [IC_{n-1,target}], [IC_{n-2,target}] \ldots [IC_{n,target}])*F_v$, where $F_v$ is total eluent flow, $F_u$ is a multidimensional function, of the pH and all of the other n–I IC, that is equal to the fraction of $F_v$ that should consist of flow containing the acidic buffer and thus $F_{v,n=acidic,target}$ is the total flow contributed by combining the flows of all the reservoirs containing $[IC_{n=acidic}]$ and $F_{v,n=basic,target}=F_v-F_{v,n=acidic,target}$ is the total flow contributed by combining the flows of all the reservoirs containing $[IC_{n=basic}]$; for the $(n-1)^{th}$ component there are four flows, two are combined to produce $F_{v,n=acidic,target}$ and the other two are combined to produce $F_{v,n=basic,target}$; thus, in the case of the first two of the four flows for the $(n-1)^{th}$ component there is associated with any point in its gradient a target concentration, $[IC_{n-1,target}]$ such that $F_{v,n-1=max,n=acidic,target}=([IC_{n-1,target}]/[IC_{n-1=max}])*F_{v,n,target}$, is the total flow contributed by combining the flows of all the reservoirs containing $[IC_{n-1=max,n=acidic}]$ and $F_{v,n-1=0,n=acidic,target} = F_{v,n,target} - F_{v,n-1=max,n=acidic,target}$ is the total flow contributed by combining the flows of all the reservoirs containing $[IC_{n-1=0,n=acidic}]$; likewise, in the case of the other two of the four flows for the $(n-1)^{th}$ component there is associated with any point in its gradient a target concentration, $[IC_{n-1,target}]$ such that $F_{v,n-1=max,n=basic,target} = ([IC_{n-1,target}]/[IC_{n-1,max}])*F_{v,n=basic,target}$ is the total flow contributed by combining the flows of all the reservoirs containing $[IC_{n-1=max,n=basic}]$ and $F_{v,n-1=0,n=basic,target} = F_{v,n=basic,target} - F_{v,n-1=max,n=basic,target}$ is the total flow contributed by combining the flows of all the reservoirs containing $[IC_{n-1=0,n=basic}]$; thus, for the $(n-2)^{th}$ component there are eight partitioned flows: $F_{v,n-2=max,n-1=max,n=acidic,target}$, $F_{v, n-2=max,n-1=0,n=acidic,target}$, $F_{v, n-2=max,n-1=max,n=basic,target}$, $F_{v, n-2=max,n-1=0,n=basic,target}$, $F_{v, n-2=0,n-1=0,n=acidic,target}$, $F_{v, n-2=0,n-1=max,n=acidic,target}$, $F_{v, n-2=0,n-1=max,n=basic,target}$, $F_{v, n-2=0,n-1=0,n=basic,target}$; and for each of the $(n-m)^{th}$ components, $n-1 \geq m \geq 0$, there are $2^{(m+1)}$ partitioned flows defined by the same ratios derived from the target concentration value of the gradient for the $(n-m)^{th}$ component; and a) connecting in series after the first column containing an anionic ion exchange stationary phase a second column containing a hydrophobic stationary phase and equilibrating the stationary phases contained in the first and second columns at the initial pH and initial concentrations of the other n−1 IC;

b) supplying to the ion exchange stationary phase contained in the first column an eluent with a variable pH starting at the initial pH and an initial IC concentration formed from the continuous mixing of (i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC; repeating (b) with a second IC and up to an nth IC to create n−1 independent gradients in n−I IC plus an independent pH gradient within the first and second columns according to the mixing algorithms detailed just above;

c) eluting the charged molecules, each of which consecutively elutes from the ion exchange stationary phase contained in the first column at its effective isoelectric point until a predetermined final pH and final n−1 IC concentrations are reached;

d) directing for secondary separation the resulting effluent containing the consecutively eluted charged molecules from the first column into the hydrophobic stationary phase contained in the second column and;

e) binding the consecutively eluted charged molecules from the first column that are sufficiently hydrophobic to the hydrophobic stationary phase contained in the second column until the predetermined final pH is reached;

f) collecting the separated molecular fractions not bound to the second column g) disconnecting, as directed by software, the first column from the second column;

h) supplying to the hydrophobic stationary phase contained in the second column an eluent with a variable pH starting at the initial pH and an initial IC concentration formed from the continuous mixing of (1i) a solution with predetermined acidic pH containing the at least one buffering component and an IC and a solution with predetermined acidic pH containing the at least one buffering component and no IC pumped out from a first pair of reservoirs and mixed so as to produce a predetermined concentration of IC and (1ii) a solution at a predetermined basic pH containing the at least one buffering component and an IC and a solution with predetermined basic pH containing the at least one buffering component and no IC pumped out from a second pair of reservoirs and mixed so as to produce the predetermined concentration of IC, wherein the mixing proportions of the solutions from the first and second pairs of reservoirs vary to maintain an unretained pH gradient with an externally defined slope and an independent and simultaneous unretained gradient in the concentration of IC; repeating (1i-1ii) with a second IC and up to an nth IC to create n−1 independent gradients in n−I IC plus an independent pH gradient to make a total of n independent gradients according to the mixing algorithms detailed just above;

i) collecting the charged molecules wherein each of the molecules consecutively elutes from the hydrophobic stationary phase contained in the second column according to the molecule's variation in hydrophobic binding free energy until a n−1 predetermined final concentrations of each of the n−1 IC is reached and a predetermined final pH is reached; and j) repeating steps a)-i) as deemed necessary to separate all of the molecular species of interest.

What is claimed is:

1. A system for separating charged molecules on the basis of their differential electrostatic binding to a charged stationary phase comprising:

a computer to control the delivery of acidic and basic pISep buffer solutions, thereby creating gradients in buffer composition;

one or more stationary phases at least one of which is predominantly anionic or cationic;

a first reservoir containing an acidic pISep buffer;

a second reservoir containing a basic pISep buffer;

a pump A;

a first fluid connecting means for connecting pump A to the first reservoir and to the one or more stationary phases, whereby the acidic pISep buffer can be withdrawn from the first reservoir and pumped onto the inlet of the one or more stationary phases;

a pump B;

a second fluid connecting means for connecting pump B to the first reservoir and to the stationary phases, whereby the basic pISep buffer can be withdrawn from the second reservoir and pumped onto the inlet of the one or more stationary phases;

one or more detectors attached to the outlet of the one or more stationary phases;

a valve system V to allow shunting of an eluent from the one or more stationary phases to or away from the next stationary phase or to a fraction collection system for collection of eluent samples;

a fraction collector for collecting eluent samples of predetermined size as they elute from the position after the eluent exits a first stationary phase and before it optionally enters a second stationary phase;

an injection system for selectively injecting one or more selected samples exiting a first stationary phase onto a second stationary phase;

a software system for controlling the injection of the one or more selected samples;

a fraction collection system for collection of eluent samples of predetermined size as they elute from the position after the eluent exits a second stationary phase;

a software system for controlling the creation of pH gradients in this system for separating charged molecules on the basis of their differential electrostatic binding to a charged stationary phase comprising:

a) GUI to allow specification and storage in memory of a pH gradient structure, linear or nonlinear such that the pH gradient structure specifies pH as a function of column volumes of eluent pumped or time;

b) an equation that specifies the relationship between the % acidic pISep buffer (A %) in the eluent stream and the pH such as: A %=$a*pH^9+b*pH^8+c*pH^7+d*pH^6+e*pH^5+f*pH^4+g*pH^3+h*pH^2+i*pH+j$ where a through j are fitting constants;

c) a communication protocol that directs pump A to pump at a rate such that throughout the operation of the system the proportion of the total fluid pumping rate, (rate of pumping acidic buffer/(rate of pumping acidic pISep buffer+rate of pumping basic pISep buffer)) that is controlled by that pump is (A % as determined by the value calculated from the pH required by the gradient structure and the equation in section b)*0.01 and pump B to pump at a rate that is a proportion of the total fluid pumping rate equal to 1−(A %*0.01);

d) a second communication protocol that directs V to shunt eluent exiting the initial stationary phase to or away from the second stationary phase based on a criterion set by the user from a set of criteria consisting of UV absorption, fluorescence, pH, refractive index, and signal peak count.

2. A system for separating charged molecules on the basis of their differential binding to at least one stationary phase comprising:

a computer to control the delivery of buffer solutions; and
at least one stationary phase; and $2^n$ reservoirs $R_1, R_2, \ldots R_{2^n-1}, R_{2^n}$, $n \geq 2$, reservoirs $R_1, R_2, \ldots R_{2^{n-1}-1}, R_{2^{n-1}}$ containing a most acidic pISep buffer isocratic in pH, reservoirs $R_{2^{n-1}+1}, R_{2^{n-1}+2}, \ldots R_{2^n-1}, R_{2^n}$ containing a most basic pISep buffer with all reservoirs isocratic in pH; and n−1 additives are distributed among the $2^n$ reservoirs; and reservoirs $R_1$, $R_2$ are such that $R_1$ contains a minimum concentration of additive 1, $R_2$ contains a maximum concentration of additive 1, reservoirs $R_3$, $R_4$ are such that $R_3$ contains a minimum concentration of additive 1, $R_4$ contains a maximum concentration of additive 1, . . . this pattern continuing in pairs to reservoirs $R_{2^n-1}, R_{2^n}$ such that $R_{2^n-1}$ contains a minimum concentration of additive 1, $R_{2^n}$ contains a maximum concentration of additive 1; and if n>2 then reservoirs $R_1, R_2, R_3, R_4$ such that $R_1, R_2$ contain a minimum concentration of additive 2, $R_3, R_4$ contains a maximum concentration of additive 2, reservoirs $R_5, R_6, R_7, R_8$ such that $R_5, R_6$ contain a minimum concentration of additive 2, $R_7, R_8$ contains a maximum concentration of additive 2, . . . continuing this pattern in pairs of pairs to $R_{2^n-3}, R_{2^n-2}, R_{2^n-1}, R_{2^n}$ such that $R_{2^n-3}, R_{2^n-2}$ contain a minimum concentration of additive 2, $R_{2^n-1}, R_{2^n}$ contain a maximum concentration of additive 2; and generally, for the $m^{th}$ additive, reservoirs $R_1, R_2, \ldots R_{2^{m-1}-1}, R_{2^{m-1}}$ contain a minimum concentration of additive m, and $R_{2^{m-1}+1}, R_{2^{m-1}+2}, \ldots R_{2^m-1}, R_{2^m}$ contain a maximum concentration of additive m, $R_{2^m+1}^m$, $R_{2^m+2}^m, \ldots ^-R_{3*2^{m-1}-1}, R_{3*2^{m-1}}$ contain a minimum concentration of additive m, and this continues until $R_{2^n-2^m+1}^n, R_{2^n-2^m+2}^n, \ldots R_{2^n-2^{m-1}-1}^n, R_{2^n-2^{m-1}}^n$ contain a minimum concentration of additive m, $R_{2^n-2^{m-1}+1}^n, R_{2^n-2^{m-1}+2}^n, \ldots R_{2^n-1}^n, R_{2^n}^n$ contain a maximum concentration of additive m; and pumps $A_1$ to $A_n$ for withdrawing fluid from the reservoirs $R_1$ to $R_n$ respectively at rates $r_1$ to $r_n$ respectively; and a valve system V to allow shunting of an eluent from any of the at least one stationary phase to or away from the next stationary phase or to or away from a fraction collection system; and a fluid conduction system, F, for mixing the fluids pumped by $A_1, A_2, \ldots A_{n-1}, A_n$ and conducting the mixed fluids into the stationary phases; and one or more detectors selected from the group consisting of detectors measuring UV absorption, visible absorption, infrared absorption, fluorescence, pH, and refractive index positioned in the eluent stream after any one or more of the set of stationary phases; and a fraction collection system for collection of eluent samples of predetermined size as they elute from the position after the eluent exits a first stationary phase and before it enters a second stationary phase; and an injection system for selectively injecting one or more selected samples exiting a first stationary phase onto a second stationary phase; and a software system for controlling the injection of the one or more selected samples; and a fraction collection system for collection of eluent samples of predetermined size as they elute from the position after the eluent exits a second stationary phase; and a software system for controlling the creation of simultaneous independent or dependent pH and additive gradients in this system for separating molecules on the basis of their differential binding to one or more stationary phases that comprises:

a. a GUI to allow specification and storage in memory of a pH gradient structure, linear or nonlinear, and specification and storage in memory of m additive solute gradient structures, $EGS_m$, m=n−1, linear or nonlinear such that the pH gradient structure specifies pH as a function of column volumes of eluent pumped or time and $EGS_m$ specifies the concentration of the $m^{th}$ additive solute, $E_m$, as a function of column volumes of eluent pumped or time such that the gradient in pH is simultaneous and independent of the n−1 additive gradients that are also simultaneously independent of each other; and b. an equation, a function of $(E_1, E_2, E_3, \ldots E_{n-2}, E_{n-1}, pH)$, that specifies the relationship between the % acidic pISep buffer (A %) in the eluent stream in the presence of n−1 additives and the pHt; and c. for the $m^{th}$ additive, $1 \leq m \leq n-1$, at any given time or column volume the concentration of the additive, in the eluent delivered to the stationary phase is determined by $EGS_m$, and, for all reservoirs, the concentration of the $m^{th}$ additive in each of the reservoirs is either the maximum for the system or the minimum for the system, thus $X_{min}(E_m)=(E_{max}-E_m)/(E_{max}-E_{min})$ is the fraction to be pumped from a reservoir containing the $E_{min}$ whereas $X_{max}(E_m)=(E_m-E_{min})/(E_{max}-E_{min})$ is the fraction to be pumped from a reservoir containing the $E_{max}$, thus the fraction of the total pumping rate to be pumped from the $k^{th}$ reservoir, $1 \leq k \leq 2^n$, is $[X_{min\ or\ max}(E_{n-1})*X_{min\ or\ max}(E_{n-2})* \ldots *X_{min\ or\ max}(E_1)*X_{min\ or\ max}(E_0)]*0.01*A\%*r_{total}$ if the $k^{th}$ reservoir is from the group of reservoirs that contain the acid pISep buffers or $[X_{min\ or\ max}(E_{n-1})*X_{min\ or\ max}(E_{n-2})*\ldots*X_{min\ or\ max}(E_1)*X_{min\ or\ max}(E_0)]*0.01*(100-A\%)*r_{total}$ if the $k^{th}$ reservoir is from the group of reservoirs that contain the basic pISep buffers; and d. communication protocols $P_k$, $1 \leq k \leq 2^n$, each of which directs its respective pump $A_k$ to pump at a rate $r_k$ as calculated according to (c) above; and e. a communication protocol $P_{mix}$ that efficiently mixes the eluent streams pumped from all of the $2^n$ reservoirs to create a single eluent stream; and f. a communication protocol $P_V$ that directs V to shunt eluent exiting the initial stationary phase to or away from a fraction collector or the second stationary phase based on one or more criteria set by the user from a set of criteria consisting of time of exit from a first stationary phase, column volume of exit from a first stationary phase, UV absorption, fluorescence, pH, refractive index, and signal peak count.

3. The system of claim 2, wherein the additive solute is a compound from the group of compounds consisting of non-ionic detergents, ionic detergents, polar organic molecules, nonpolar organic molecules, acids, bases, neutral salts, acidic salts and basic salts.

4. The system of claim 2 where the function of $(E_1, E_2, E_3, \ldots E_{n-2}, E_{n-1}, pH)$, that specifies the relationship between the % acidic pISep buffer (A %) in the eluent stream in the presence of n−1 additives and the pH, is of the form: $A\% = a_p*E_1^p + a_{p-1}*E_1^{p-1} + \ldots + *E_1 + a_0$, p an integer>0, where $a_p$ through $a_0$ are each distinct functions of $(E_2, E_3, \ldots E_{n-2}, E_{n-1}, pH)$; and a. each of the $a_p, a_{p-1}, \ldots a_1, a_0$ are of the form: $b_{q(w)}*E_2^{q(w)} + b_{q(w)-1}*E_2^{q(w)-1} + \ldots + b_1*E_2 + b_0$, where each q(w) is a distinct integer>0 for all integral w from 0 to p, and where $b_{q(w)}$ through $b_0$ are each distinct functions of $(E_3, E_4, \ldots E_{n-2}, E_{n-1}, pH)$; and b. this pattern is repeated with each coefficient of each power of the $m^{th}$ additive a distinct function of $(E_{m+1}, E_{m+2}, \ldots E_{n-2}, E_{n-1}, pH)$ each of which is in the form of a polynomial in the concentration of the $(m+1)^{th}$ additive with coefficients that are functions of the concentrations of the $(m+2)^{th}$ to the $(n-1)^{th}$ additives plus pH; and c. the coefficients of the polynomials in the concentration of $(n-1)^{th}$ additive are purely functions of pH of the form: $k_{z,j}*pH^j + k_{z,j-1}*pH^{j-1} + \ldots + k_{z,1}*pH + k_{z,0}$, and all $k_{z,x}$ are fitting constants where each z represents one of the set of the coefficients of the polynomials in the concentration of the $(n-1)^{th}$ additive and there is one and only one distinct z for each such coefficient.

5. A system for separating charged molecules on the basis of their differential binding to at least one stationary phase comprising:

A computer to control the delivery of buffer solutions; and at least one stationary phase; and $2^n$ reservoirs $R_1, R_2, \ldots R_{2^n-1}, R_{2^n}$, $n \geq 2$; and n additives distributed among the $2^n$ reservoirs; and reservoirs $R_1, R_2$ are such that $R_1$ contains a minimum concentration of additive 1, $R_2$ contains a maximum concentration of additive 1, reservoirs $R_3, R_4$ are such that $R_3$ contains a minimum concentration of additive 1, $R_4$ contains a maximum concentration of additive 1, ... this pattern continuing in pairs to reservoirs $R_{2^n-1}, R_{2^n}$ such that $R_{2^n-1}$ contains a minimum concentration of additive 1, $R_{2^n}$ contains a maximum concentration of additive 1; and if n>2 then reservoirs $R_1, R_2, R_3, R_4$ such that $R_1, R_2$ contain a minimum concentration of additive 2, $R_3, R_4$ contains a maximum concentration of additive 2, reservoirs $R_5, R_6, R_7, R_8$ such that $R_5, R_6$ contain a minimum concentration of additive 2, $R_7, R_8$ contains a maximum concentration of additive 2, ... continuing this pattern in pairs of pairs to $R_{2^n-3}, R_{2^n-2}, R_{2^n-1}, R_{2^n}$ such that $R_{2^n-3}, R_{2^n-2}$ contain a minimum concentration of additive 2, $R_{2^n-1}, R_{2^n}$ contain a maximum concentration of additive 2; and generally, for the $m^{th}$ additive, reservoirs $R_1, R_2, \ldots R_{2^{m-1}-1}, R_{2^{m-1}}$ contain a minimum concentration of additive m, and $R_{2^{m-1}+1}, R_{2^{m-1}+2}, \ldots R_{2^m-1}, R_{2^m}$ contain a maximum concentration of additive m, $R_{2^m+1}, R_{2^m+2}, \ldots R_{3*2^{m-1}-1}, R_{3*2^{m-1}}$ contain a minimum concentration of additive m, and this continues until $R_{2^n-2^m+1}, R_{2^n-2^m+2}, \ldots R_{2^n-2^{m-1}-1}, R_{2^n-2^{m-1}}$ contain a minimum concentration of additive m, $R_{2^n-2^{m-1}+1}, R_{2^n-2^{m-1}+2}, \ldots R_{2^n-1}, R_{2^n}$ contain a maximum concentration of additive m; and pumps $A_1$ to $A_n$ for withdrawing fluid from the reservoirs $R_1$ to $R_n$ respectively at rates $r_1$ to $r_n$ respectively; and a valve system V to allow shunting of an eluent from any of the at least one stationary phase to or away from the next stationary phase or to or away from a fraction collection system; and A fluid conduction system, F, for mixing the fluids pumped by $A_1, A_2, \ldots A_{n-1}, A_n$ and conducting the mixed fluids into the stationary phases; and one or more detectors selected from the group consisting of detectors measuring UV absorption, visible absorption, infrared absorption, fluorescence, pH, and refractive index positioned in the eluent stream after any one or more of the set of stationary phases; and a fraction collection system for collection of eluent samples of predetermined size as they elute from the position after the eluent exits a first stationary phase and before it enters a second stationary phase; and an injection system for selectively injecting one or more selected samples exiting a first stationary phase onto a second stationary phase; and a software system for controlling the injection of the one or more selected samples; and optionally a fraction collection system for collection of eluent samples of predetermined size as they elute from the position after the eluent exits a second stationary phase; and a software system for controlling the creation of simultaneous independent or dependent additive gradients in this system for separating molecules on the basis of their differential binding to one or more stationary phases that comprises:

a. a GUI to allow specification and storage in memory of a pH gradient structure, linear or nonlinear, and specification and storage in memory of m additive solute gradient structures, $EGS_m$, m=n, linear or nonlinear such that each $EGS_m$, specifies the concentration of the $m^{th}$ additive solute, $E_m$, as a function of column volumes of eluent pumped or time such that each of the gradients in each of the n additives is simultaneous and independent of the other n−1 additive gradients that are also simultaneously independent of each other; and b. for the $m^{th}$ additive, $1 \leq m \leq n$, at any given time or column volume the concentration of the additive, in the eluent delivered to the stationary phase is determined by $EGS_m$, and, for all reservoirs, the concentration of the $m^{th}$ additive in each of the reservoirs is either the maximum for the system or the minimum for the system, thus $X_{min}(E_m) = (E_{max} - E_m)/(E_{max} - E_{min})$ is the fraction to be pumped from a reservoir containing the $E_{min}$ whereas $X_{max}(E_m) = (E_m - E_{min})/(E_{max} - E_{min})$ is the fraction to be pumped from a reservoir containing the $E_{max}$, thus the fraction of the total pumping rate to be pumped from the $k^{th}$ reservoir, $1 \leq k \leq 2^n$, is $[X_{min\ or\ max}(E_{n-1})*X_{min\ or\ max}(E_{n-2})* \ldots *X_{min\ or\ max}(E_1)*X_{min\ or\ max}(E_0)]*r_{total}$, where $r_{total}$ is $\Sigma r_n$; and c. communication protocols $P_k$, $1 \leq k \leq 2^n$, each of which directs its respective pump $A_k$ to pump at a rate $r_k$ as calculated according to (b) above; and d. a communication protocol $P_{mix}$ that efficiently mixes the eluent streams pumped from all of the $2^n$ reservoirs to create a single eluent stream; and e. a communication protocol $P_V$ that directs V to shunt eluent exiting the initial stationary phase to or away from a fraction collector or the second stationary phase based on one or more criteria set by the user from a set of criteria consisting of time of exit from a first stationary phase, column volume of exit from a first stationary phase, UV absorption, fluorescence, pH, refractive index, and signal peak count.

6. The system of claim 5, wherein the additive solute is a compound from the group of compounds consisting of non-ionic detergents, ionic detergents, polar organic molecules, nonpolar organic molecules, acids, bases, neutral salts, acidic salts nd basic salts.

* * * * *